(12) United States Patent
Tsujii et al.

(10) Patent No.: US 6,279,388 B1
(45) Date of Patent: Aug. 28, 2001

(54) APPARATUS FOR CALIBRATING HARDNESS TESTER, METHOD FOR CALIBRATING THE SAME AND APPARATUS FOR EVALUATING DYNAMIC CHARACTERISTIC OF SPECIMEN

(75) Inventors: Masaharu Tsujii; Fumihiko Koshimizu, both of Zama (JP)

(73) Assignee: Akashi Corporation, Kanagawa-ken (JP)

( * ) Notice: Subject to any disclaimer, the term of this patent is extended or adjusted under 35 U.S.C. 154(b) by 0 days.

(21) Appl. No.: 09/276,815

(22) Filed: Mar. 26, 1999

(30) Foreign Application Priority Data

Apr. 6, 1998 (JP) .................................................. 10-110140
Jul. 3, 1998 (JP) .................................................. 10-204376
Jul. 15, 1998 (JP) .................................................. 10-200791

(51) Int. Cl.⁷ .................................................. G01B 11/22
(52) U.S. Cl. .................................................. 73/82
(58) Field of Search .................................................. 73/81, 82

(56) References Cited

U.S. PATENT DOCUMENTS 4,820,051 * 4/1989 Yanagisawa et al. ...................... 73/81
5,377,697 * 1/1995 Deutsch et al. ........................... 73/81
5,616,857 * 4/1997 Merck, Jr. et al. ........................ 73/82

* cited by examiner

Primary Examiner—Robert Raevis
(74) Attorney, Agent, or Firm—Oliff & Berridge, PLC.

(57) ABSTRACT

A method for calibrating an apparatus for calibrating a hardness tester, the method comprising the steps of: setting a plurality of calibration points between a rated force point at which a rated force of a force measuring member is applied and a zero point at which no-load is applied, for measuring outputs (mV/V) from the force measuring member according to test forces(N) applied to the force measuring member; and calculating a relation between the test forces(N) and the outputs(mV/V) as an approximation based on the test forces(N) and the outputs(mV/V) according to the test forces(N) at the calibration points. An apparatus for evaluating a dynamic characteristic of a specimen, which installed in a hardness tester, the apparatus comprising: a force measuring member; a force transmitting portion which is movable up and down; a distance measuring member incorporated in the force transmitting portion to be contacted with the force measuring member from above; and an indenter.

6 Claims, 18 Drawing Sheets

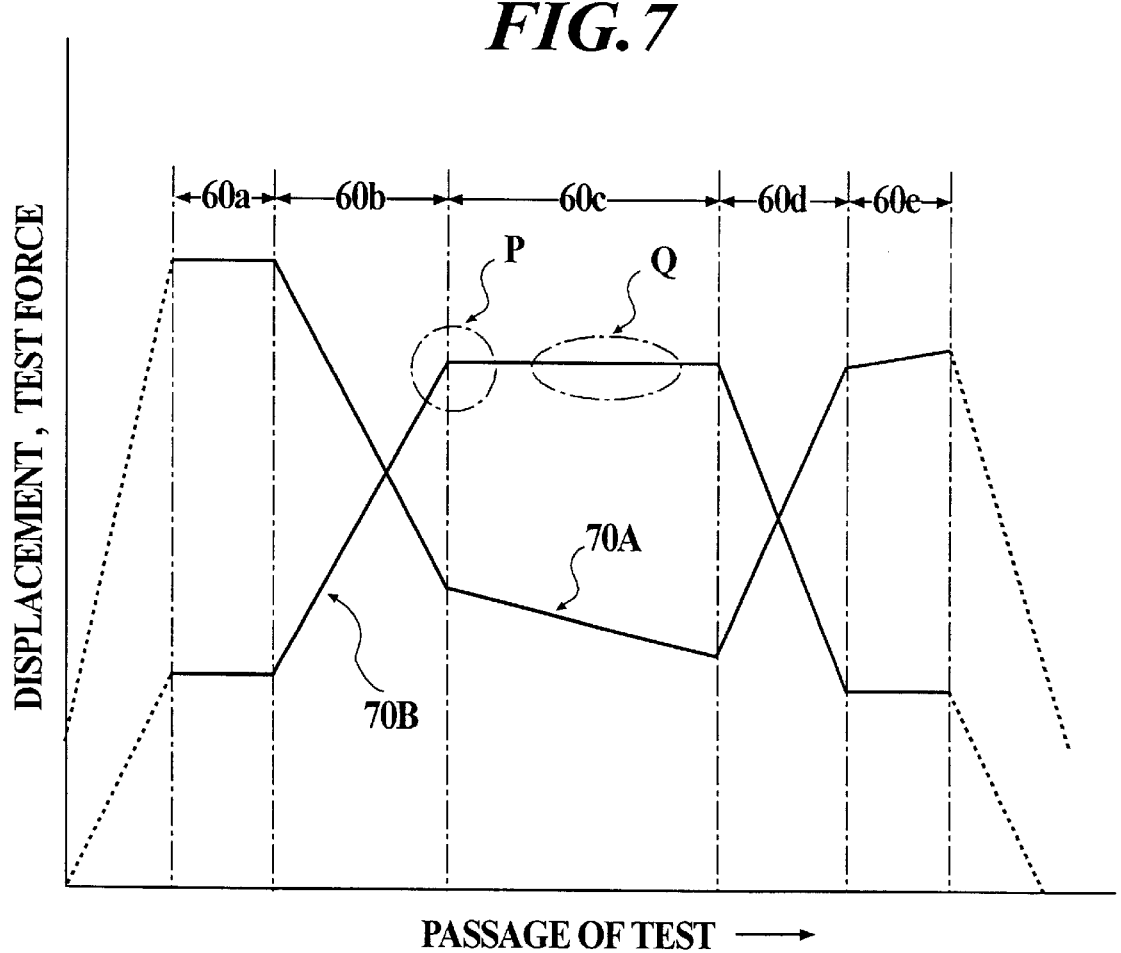

APPARATUS FOR CALIBRATING HARDNESS TESTER, METHOD FOR CALIBRATING THE SAME AND APPARATUS FOR EVALUATING DYNAMIC CHARACTERISTIC OF SPECIMEN

BACKGROUND OF THE INVENTION

1. Field of the Invention

The present invention relates to an apparatus for calibrating a hardness tester, a method for calibrating the apparatus and a hardness tester and an apparatus for evaluating a dynamic characteristic of a specimen.

2. Description of Related Art

Generally, hardness evaluation, that is, a hardness test for a specimen by a hardness tester is carried out by measuring a force applied to the specimen and a deformed amount of the specimen with applying the force.

With the hardness test for a specimen, static characteristic evaluation, that is, a static test, and dynamic characteristic evaluation, that is, a dynamic test are included. With the static characteristic evaluation, a force is applied to a specimen, then a deformation thereof is ended, thereafter a deformed amount of the specimen is measured. Then, the relation between the force and the deformed amount of the specimen is evaluated.

On the other hand, with the dynamic characteristic evaluation, when a specimen is deforming gradually by output forces, that is, applied forces from the hardness tester, it is evaluated that the relation between the forces applied to the specimen at each point and deformed amounts of the specimen at each point.

However, according to a conventional hardness tester, it is not possible to carry out the dynamic test but to carry out only the static test.

Next, a calibration for the hardness tester will be explained. As shown in FIG. 20, a force meter 202 and a dial master gage 203 are incorporated in series in a hardness tester 1. When a test force is applied, the test force is measured by the force meter 202, a displacement is measured by the dial master gage 203, and an indicated value on a displacement gage 4 which is incorporated in the hardness tester 1 is read.

The operation is repeated for several times by changing the test forces. The indicated values on the dial master gage 203 and the displacement gage 4 with each test force are filled in a measurement data chart 205, so that the hardness tester is calibrated based on the values filled in the measurement data chart 205.

The calibration above-described is the static test. Therefore, there is a problem that for carrying out the dynamic test, it is required to carry out the static test for several times by changing the test forces.

SUMMARY OF THE INVENTION

The present invention was developed in view of the above-described problems. Therefore, an object of the present invention is to provide a method for calibrating an apparatus for calibrating a hardness tester, which can prevent causing error with a dynamic test, which occurs by hysteresis of the force(load) measuring member and repeating with the dynamic test. An another object of the present invention is to provide an apparatus for calibrating a hardness tester, which can statically and dynamically evaluate test forces and deformed amounts of a specimen according to the applied test forces, which are required to calibrate the hardness tester. A further object of the present invention is to provide an apparatus for evaluating a dynamic characteristic of a specimen, which can evaluate a dynamic characteristic of a specimen.

In order to accomplish the above-described objects, in one aspect of the present invention, a method for calibrating an apparatus for calibrating a hardness tester, the method comprises the steps of: setting a plurality of calibration points between a rated force point at which a rated force of a force(load) measuring member is applied and a zero point at which no-load is applied, for measuring outputs (mV/V) from the force measuring member according to test forces (N) applied to the force measuring member; and calculating a relation between the test forces(N) and the outputs(mV/V) as an approximation based on the test forces(N) and the outputs(mV/V) according to the test forces(N) at the calibration points.

The calibration points can be set between the rated force point and the zero point to have same intervals each other.

For the hardness tester, the Rockwell hardness tester, the Vickers hardness tester, the Brinell hardness tester or the like can be applied, however, another tester which can apply a desired force to a force(load) transmitting portion can be applied.

For the force measuring member, a load cell can be usually employed, however, another member which can measure the force applied thereto can be employed.

At the rated force point, for example, when the rating of the force measuring member is 2 kN, the test force of 2 kN is applied to the force measuring member.

According to the calibrating method of the invention, the apparatus for calibrating a hardness tester is installed in the commercial hardness tester, so that it is possible to calibrate the apparatus in the same way as that of the ordinary hardness test.

Further, in addition to the rated force point and the zero point, because it can be set a number of calibration points between them, it can be possible to prevent causing error with a dynamic test, which occurs by hysteresis of the force measuring member and by repeating with the dynamic test.

In accordance with another aspect of the present invention, an apparatus for calibrating a hardness tester, which installed in a hardness tester, the apparatus comprises: a bottom frame to be mounted to the hardness tester; a force(load) measuring member disposed on an inner surface of the bottom frame; a force(load) transmitting portion which is movable up and down; a distance measuring member incorporated in the force transmitting portion to be contacted with the force measuring member from above; and a dummy indenter disposed to project in an upper end portion of the force transmitting portion to be inserted into a mounting hole for an indenter of the hardness tester. The force transmitting portion can be supported by a supporting means.

The bottom frame can have, for example, a U-like shape in cross-section and be mounted to a mounting portion for an anvil of the hardness tester. The hardness tester can be the one above-described. For the force measuring member, a load cell can be usually employed, however, another member which can continuously measure the forces applied thereto can be employed. The distance measuring member can be, for example, a laser displacement meter which continuously measures a distance between a fixed point of the laser displacement meter and a point of the force transmitting portion. Deformed amounts of the force measuring member can be measured as the distance. For the supporting means, for example, a plurality of pillars mounted to the bottom frame can be applied. However, it is not limited to them, for example, an air bearing which supports a position of an axis by applying air at a constant pressure between the axis and a cylinder, or the like can be applied. With the air bearing, a friction drag which the axis received can be extremely small.

According to the apparatus of the invention, because it is possible to continuous measure the forces and deformed amounts of the force measuring member according to the applied test forces, it is possible to evaluate the dynamic characteristic of the force measuring member. Further, it is possible to easily install the apparatus to the mounting portion for the anvil of the tester, and the dummy indenter is inserted into the mounting hole for an indenter of the tester at the time, it is also possible to certainly mount the apparatus to the tester.

The apparatus can further comprise a preload member to press the force measuring member through the force transmitting portion. The preload member can, for example, comprise a clamping screw, a plate-like member, axes or the like. The clamping screw can be connected to the force transmitting portion through the plate-like member, so that when the clamping screw is clamped, it can be possible to apply a predefined force to the force measuring member through the force transmitting portion.

According to the apparatus, because the force measuring member can be pressed by the preload member, it can be possible to mount the apparatus to the tester in the state of applying the predefined force to the force measuring member. The preload member can be used as a force removing member when the force measuring member is exchanged.

The apparatus can further comprise a data processing equipment to which signals of the distance measuring member and the force measuring member are input and which evaluates test forces and deformed amounts according to the test forces when the test forces are changed.

The data processing equipment can be, for example, a micro computer. The data processing equipment can be connected to the force measuring member and the distance measuring member through, for example, cables, respectively, so that it can be possible to input the measured values of forces by the force measuring member and the measured values of distances measured by the distance measuring member.

According to the apparatus, because each detected signal from the distance measuring member and the force measuring member can be input to the data processing equipment, and the test forces and the deformed amounts according to the test forces can be evaluated with changing the test forces by the data processing equipment, it can be possible to carry out the dynamic evaluation.

Further, the force when the predefined test force is applied and the deformed amount according to the test force can be calculated by the data processing equipment, so that it can be possible to carry out the static evaluation based on the calculated value.

According to the apparatus, because the dynamic characteristic of the force measuring member can be evaluated, it is possible to calibrate the hardness tester.

In accordance with further aspect of the present invention, an apparatus for evaluating a dynamic characteristic of a specimen, which is installed in a hardness tester having a force (load) applying member and a specimen table, the apparatus comprises: an indenter; a force(load) transmitting portion for transmitting a force which is applied to the indenter by the force applying member to make the indenter press the specimen placed on the specimen table; a force (load) measuring member for continuously determining forces of $\alpha$ applied to the specimen from the indenter; and a distance measuring member for continuously determining deformed amounts of h of the specimen in an acting direction of the forces of $\alpha$; wherein a movable portion which includes the force transmitting portion, the force measuring member and the indenter is movable as a whole in an acting direction of the force which is applied by the force applying member, and during the movable portion is moved by being applied the force from the force applying member through the force transmitting portion and a indentation is formed in the specimen by the indenter, the apparatus carries out an evaluation of the dynamic characteristic of the specimen based on: continuous values of the forces of $\alpha$ which are determined based on measured values measured continuously by the force measuring member; and continuous values of the deformed amounts of h which are determined based on measured values measured continuously by the distance measuring member.

The hardness tester and the force measuring member can be the one above-described. The distance measuring member can be, for example, a laser displacement meter. The apparatus for evaluating a dynamic characteristic of a specimen is principally installed in such hardness testers.

In an top end portion of the force applying member of the hardness tester, for example, a dummy indenter is attached. The force transmitting portion comprises, for example, a force (load) receiving portion to receive a force from the dummy indenter. The force receiving portion has a shape which fits the dummy indenter to suitably receive the force from the dummy indenter. The dummy indenter does not have an object to make a deformation in the force receiving portion, so that a top end portion of the indenter has, for example, a hemispherical shape.

The indenter of the apparatus has, for example, a pyramidal shape. The top of the pyramidal shape, that is, the top end portion of the indenter is brought into contact to the specimen. The indenter is for causing a deformation in the specimen, that is, making a indentation, by being pressed the top end portion thereof against the specimen. The indenter can have, for example, a conical shape, a spherical shape in the top end portion or the like.

It is assumed that each constituent element or member placed between the force applying member and the specimen table, of the hardness tester, which is applied the force by the force applying member except the force measuring member and the specimen has larger hardness compared to the force measuring member and the specimen. Accordingly, it is assumed that only the force measuring member and the specimen are caused deformations by the force.

According to the apparatus of the invention, because the movable portion is moved by being applied the force from the force applying member through the force transmitting portion and the indenter presses the specimen placed on the specimen table, it is possible to form a indentation in the specimen. During the indentation is formed, it is possible to determine the continuous values of the forces of $\alpha$ which are applied to the specimen by the indenter based on the measured values measured continuously by the force measuring member. It is possible to determine the continuous values of the deformed amounts of h of the specimen in the acting direction of the forces of $\alpha$ based on the measured values measured continuously by the distance measuring member. Accordingly, by applying the force to the force transmitting portion from the force applying member of the hardness tester, subsequently applying the force to the specimen through the indenter, it is possible to determine the relation between the forces of α applied to the specimen when the specimen is gradually deformed and the deformed amounts of h of the specimen according to the forces of α. Therefore, it is possible to evaluate the dynamic characteristic of the specimen.

A load cell as the force measuring member can be disposed between the force transmitting portion and the indenter, a laser displacement meter as the distance measuring member can be disposed in the force transmitting portion, variations of ΔD of distances of D can be continuously determined by continuously measuring the distances of D between a fixed point of the laser displacement meter and a point of the force transmitting portion, and the deformed amounts of h can be continuously determined by subtracting deformed amounts of h' of the load cell in the acting direction from the variations of ΔD.

The fixed point of the laser displacement meter and the point of the force transmitting portion can be disposed in a straight line in the acting direction.

It can be preferable that the dynamic characteristic of the load cell is evaluated in advance and the deformed amounts of h' of the load cell when the forces are applied thereto are known.

The measuring of the deformed amount of h' of the load cell can be carried out, for example, by using an indenter which has plane surface in place of the indenter, which is contacted to the specimen table with the plane surface and in a state of removing the specimen. In this state, when the force is applied to the force transmitting portion by the hardness tester, the variations of the distances between the fixed point of the laser displacement meter and the point of the force transmitting portion can be continuously measured. At this time, it can be assumed that only the load cell is deformed, the measured values can be regarded as the deformed amounts of h' of the load cell, which are continuously measured in the acting direction.

Then, the dynamic characteristic of the load cell can be evaluated by a relation between the deformed amounts of h' of the load cell and the forces applied to the load cell, which are continuously measured respectively.

According to the apparatus of the invention, because the distance measuring member can be the laser displacement meter of which position is fixed, when the hardness tester applies force to the force transmitting portion, the force transmitting portion can be gradually moved relative to the laser displacement meter in the acting direction. That is, the distance of D between the fixed point of the laser displacement meter and the point of the force transmitting portion can be gradually changed. It can be possible to determine the variations of ΔD of the distance of D by continuously measuring the distance of D The variations of ΔD can be the same values as a length of the sum of the deformed amounts of h of the specimen and the deformed amounts of h' of the load cell, so that it can be possible to continuously determine the deformed amounts of h of the specimen by subtracting the deformed amounts of h' from the variations of ΔD.

The apparatus can further comprise a position adjusting member to adjust a position of the movable portion. The position adjusting member can comprise a receiving plate, a clamping screw, a plate-like member, an arm portion, axes, a concave spherical washer, a convex spherical washer or the like.

The movable portion can be, for example, movably connected by the second axis to one end portion of the arm portion which can pitch pivotally on the first axis and a guiding member for guiding the movable portion can be disposed around the movable portion, so that the movable portion can be freely moved and returned by the pitch of the arm portion with no changing the direction thereof.

To the other end portion of the arm portion, for example, the plate-like member can be attached. The clamping screw can be connected to the plate-like member and a screw portion of the clamping screw can be screwed to the receiving plate of which the position can be fixed. Accordingly, when the screw is clamped or loosened, it can be possible to pitch the arm portion.

In a connecting portion between the clamping screw and the arm portion, for example, it can employ the concave spherical washer and the convex spherical washer, and these can rotatably move to each other.

According to the apparatus of the invention, it can be possible to make the movable portion move and return by the position adjusting member. Accordingly, when the specimen is placed on the specimen table, it can be possible to apply the position adjusting member to make a space between the specimen table and the indenter, which is larger than a size of the specimen. Further, after the specimen is placed thereon, it can be possible to apply the position adjusting member to bring into contact the indenter to the specimen, so that it can be possible to easily place the specimen and prepare for the evaluation.

The force measuring member can be held by a holder which is detachably attached to the force transmitting portion, the holder can be energised by an energising member to make the force measuring member be always contacted with the force transmitting portion.

The holder can have, for example, a concave portion opening to an upper portion and approximately U-like shape in cross section. The load cell can be held in such holder.

For the energising member, for example, a helical coil spring can be applied. In this case, holding portions can be disposed to project to outer sides in the force transmitting portion and the holder, and the helical coil spring can be hooked to the holding portions to bridge them in a state of having tension. Accordingly, it can be possible to energise the holder against the force transmitting portion.

According to the apparatus of the invention, because the holder can be energised against the force transmitting portion by the energising member, it can be possible to make the force measuring member held in the holder contact to the force transmitting portion. Further, even if the force measuring member is deformed by being applied the force, it can be possible to energise the holder and the force measuring member against the force transmitting portion by the energising member with the deformation of the force measuring member. Therefore, it can be always possible to make the force measuring member contact to the force transmitting portion.

When the holder is moved in a direction of moving far away from the force transmitting portion against the energising force of the energising member, it can be possible to make a space between the force measuring member and the force transmitting portion and, for example, it can be possible to exchange the force measuring member.

The apparatus can further comprise a data processing equipment which draws up a graph showing a relation between the forces of a and the deformed amounts of h based on the measured values of the forces measured by the force measuring member and the measured values of distances of D measured by the distance measuring member.

The data processing equipment can be, for example, the one above-described.

In the data processing equipment, for example, the data of the deformed amounts of h' of the force measuring member, which can be measured in advance can be memorized. In this case, the computer can be programmed to calculate to continuously determine the deformed amount of h by subtracting the deformed amounts of h' from the variations of ΔD.

According to the apparatus of the invention, it can be possible to draw up the graph showing the relation between the forces of α applied to the specimen and the deformed amounts of h of the specimen.

BRIEF DESCRIPTION OF THE DRAWINGS

The above and other objects, features and advantages of the invention will become more apparent from the following description taken in conjunction with the accompanying drawings wherein like references refer to like parts and wherein:

FIG. 7 is a graphical representation displayed on a display portion of the calibration apparatus shown in FIG. 1, according to an example in the first embodiment;

PREFERRED EMBODIMENT OF THE INVENTION

Figure 1:
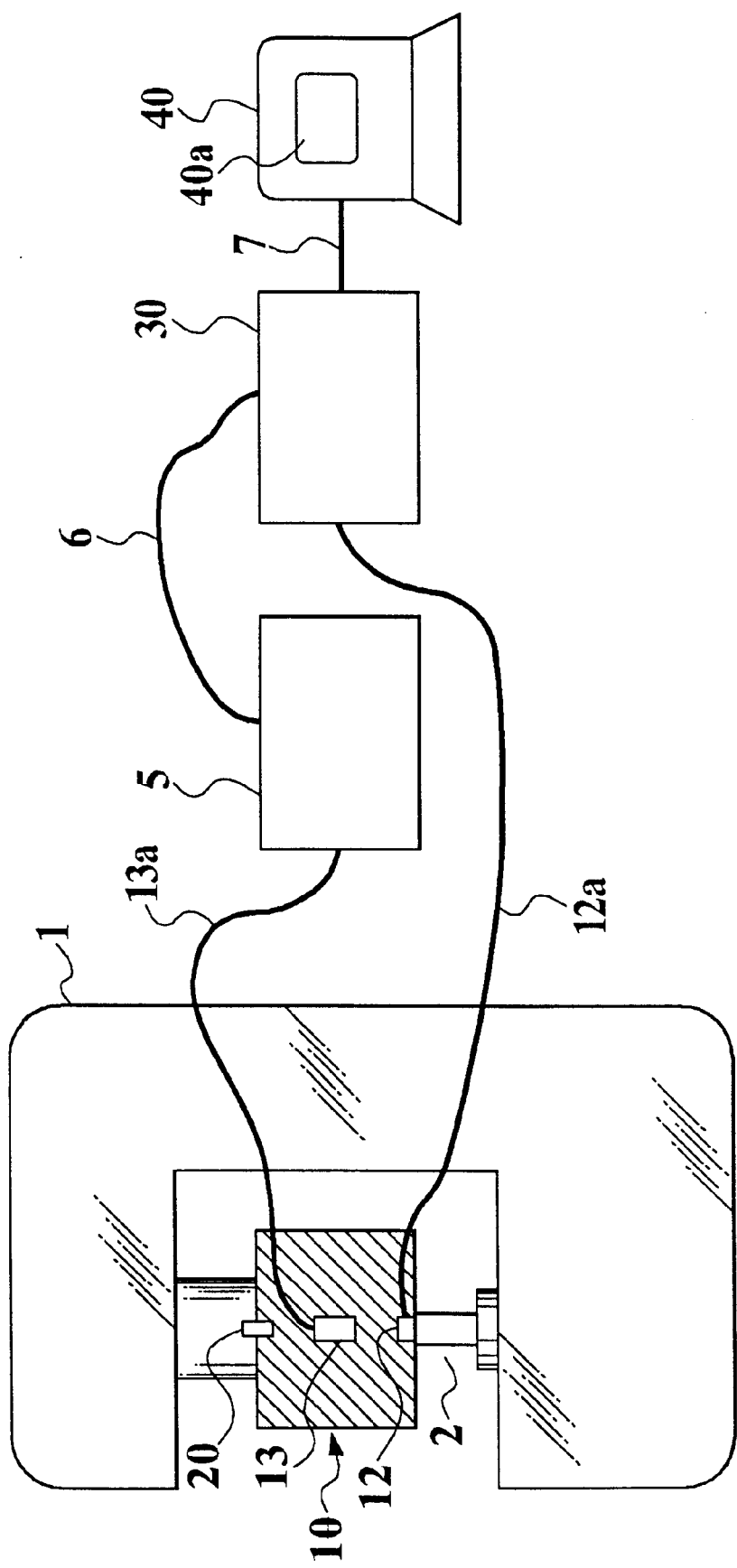
FIG. 1 is a schematic illustration of whole constitution of a calibration apparatus for the Rockwell hardness tester according to the first embodiment of the present Invention.
Figure 2:
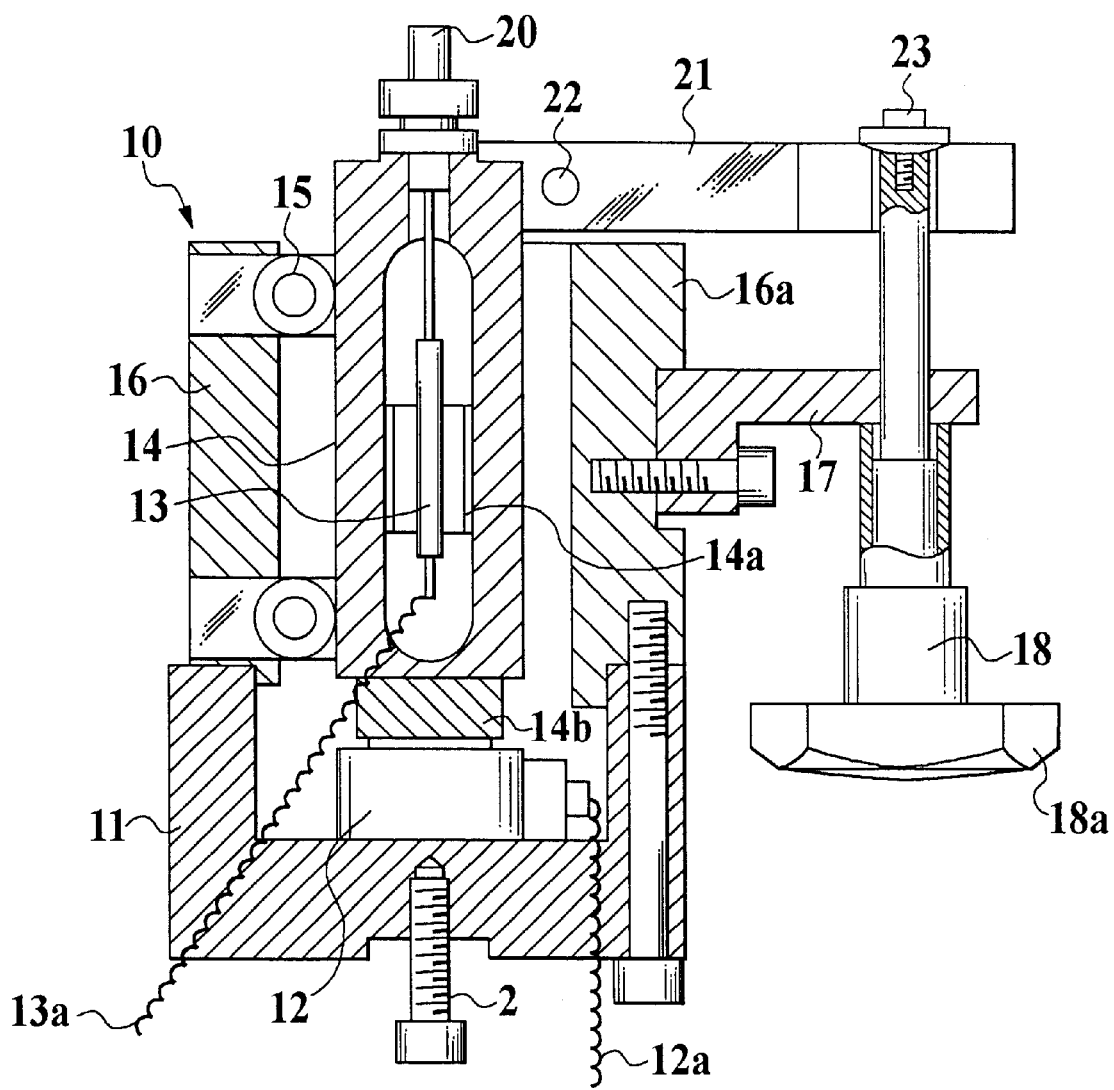
FIG. 2 is a vertical cross-sectional view of a calibration unit shown in FIG. 1.
Figure 3:
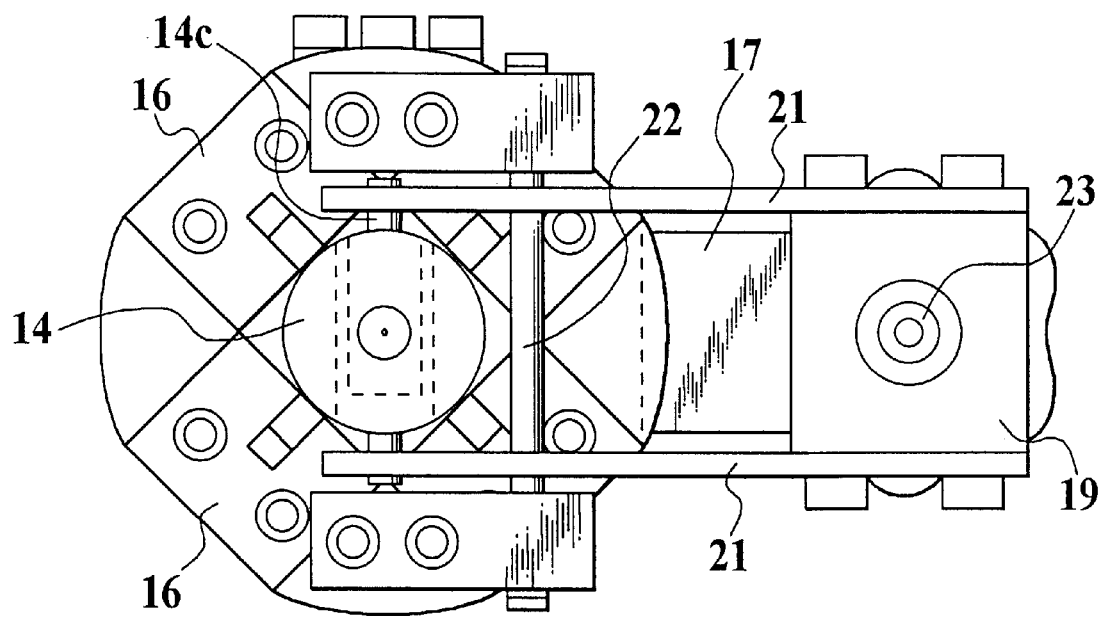
FIG. 3 is a plan view of the calibration unit shown in FIG. 2.
Figure 4:
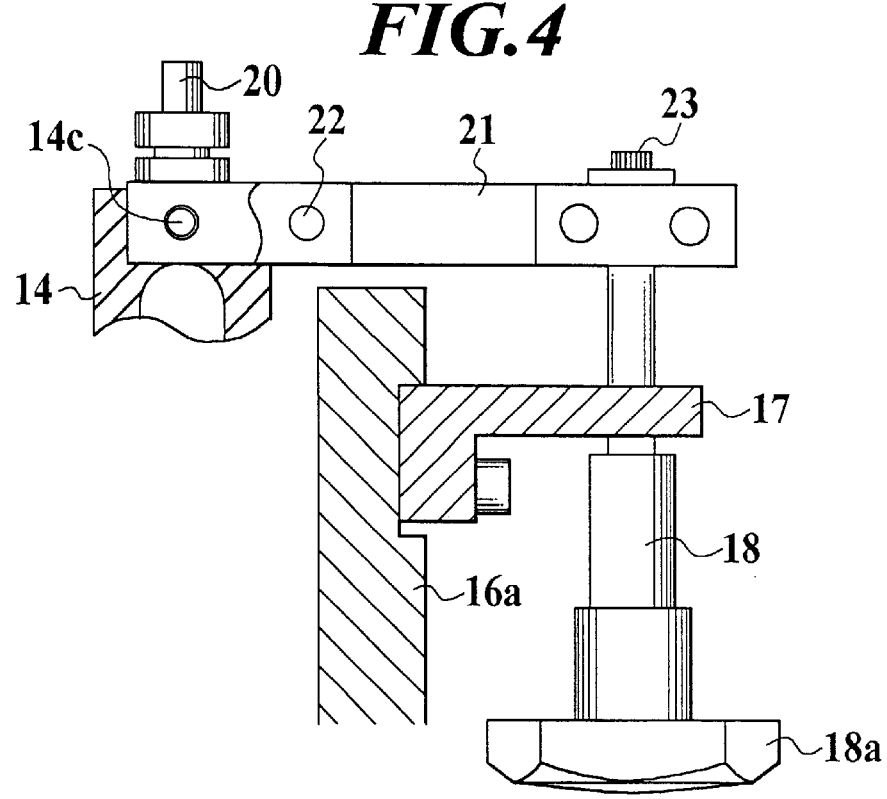
FIG. 4 is a partial front view of the calibration unit shown in FIG. 2.
Figure 5:
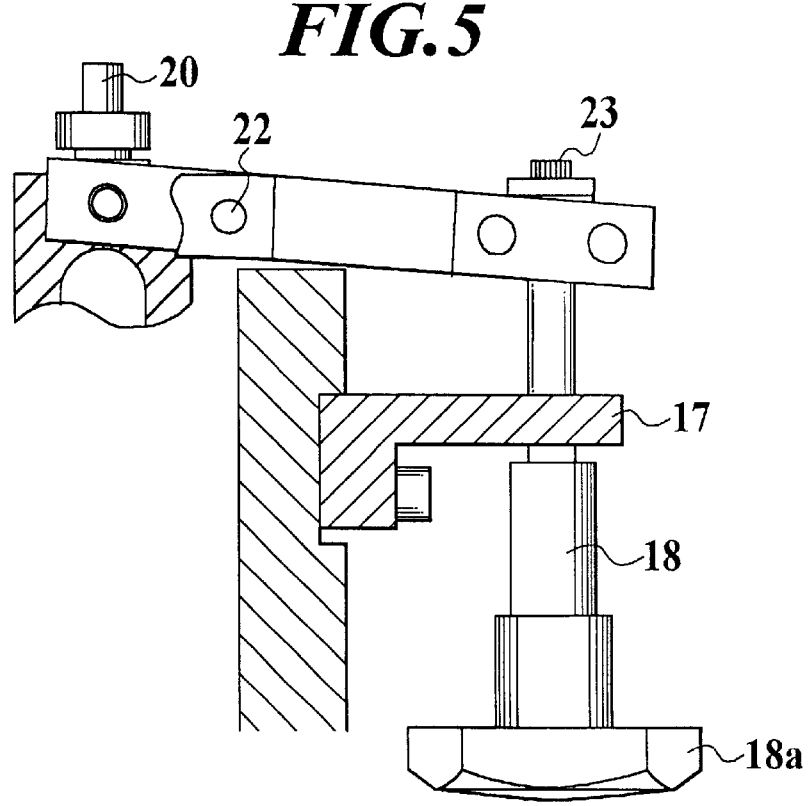
FIG. 5 is a partial front view of the calibration unit shown in FIG. 2.
Figure 6:
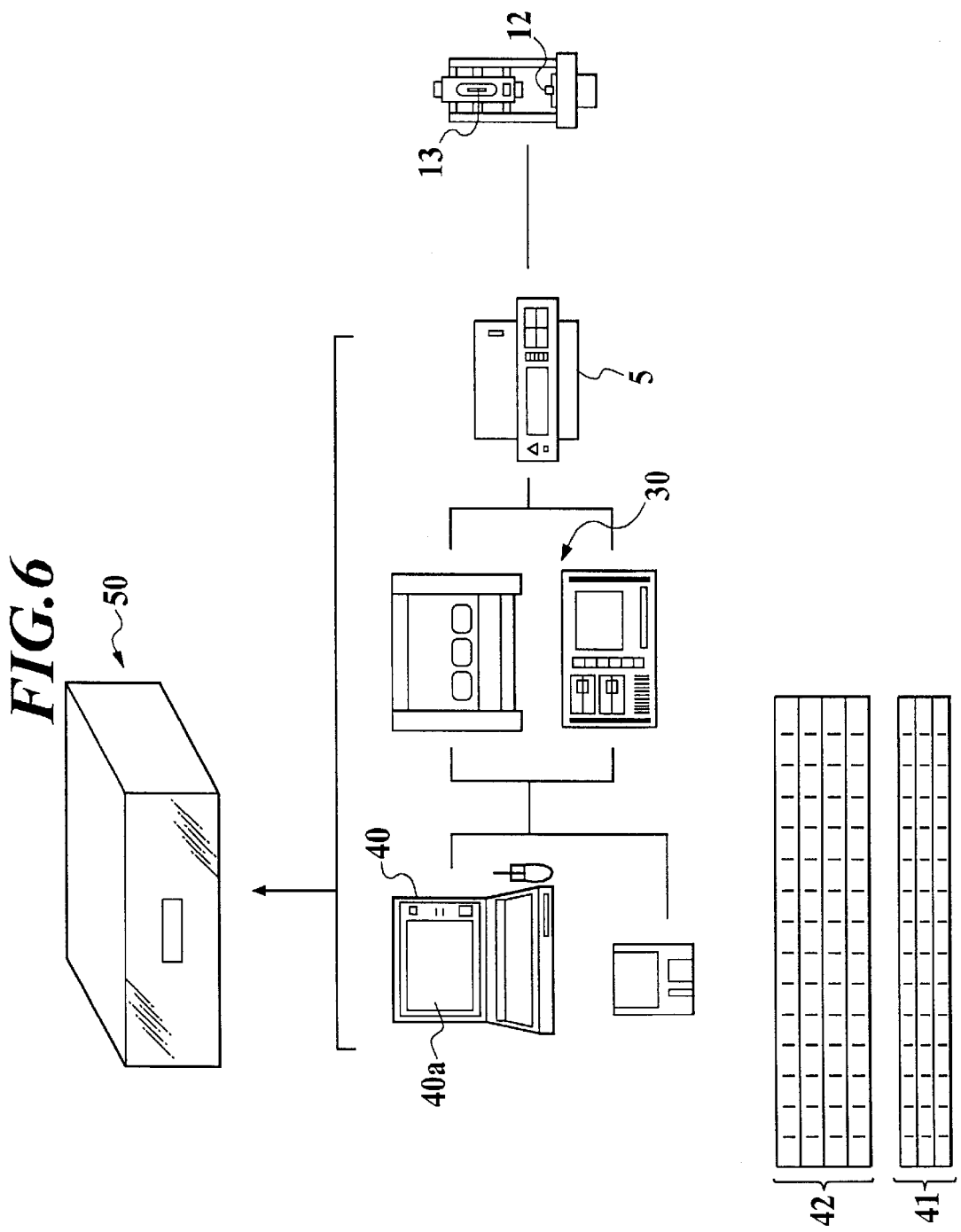
FIG. 6 is a schematic illustration explaining the calibration by the calibration apparatus shown in FIG. 1.
Figure 8A:
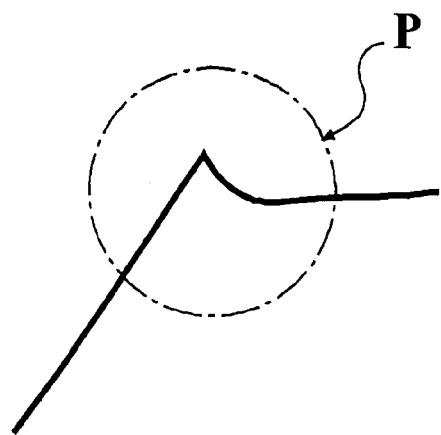
FIG. 8A is an enlarged view showing a portion indicated by an arrow P shown in FIG. 7 when the calibration is incorrect.
Figure 8B:
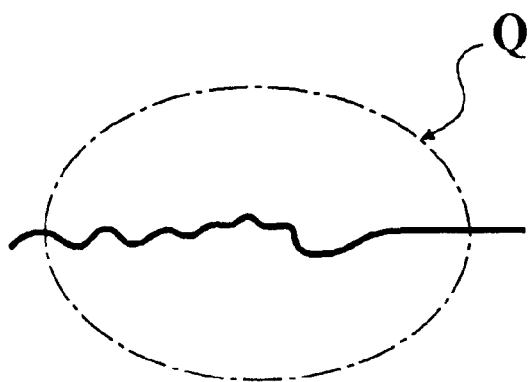
FIG. 8B is an enlarged view showing a portion indicated by an arrow Q shown in FIG. 7 when the calibration is incorrect.

Referring now to FIGS. 1 to 8B, the calibration apparatus for the Rockwell hardness tester and the calibration unit thereof according to the first embodiment of the present invention will be described as follows. FIG. 1 is a schematic illustration of whole constitution of the calibration apparatus; FIG. 2 is a vertical cross-sectional view of the calibration unit; FIG. 3 is a plan view thereof; FIGS. 4 and 5 are partial front views thereof; FIG. 6 is a schematic illustration explaining the calibration by the calibration apparatus; FIG. 7 is a graph displayed on a display portion of the calibration apparatus; FIG. 8A is an enlarged view showing a portion indicated by an arrow P shown in FIG. 7 when the calibration is incorrect; and FIG. 8B is an enlarged view showing a portion indicated by an arrow Q shown in FIG. 7 when the calibration is incorrect.

In FIG. 1, reference numeral 1 denotes the Rockwell hardness tester, therefrom an anvil and an indenter are removed and the calibration unit 10 is installed to the hardness tester 1. The calibration apparatus comprises the calibration unit 10, an amplifier 5 connected to a distance measuring member, for example, a laser displacement meter 13 in the unit 10 through a cable 13a, a data recorder 30 which is connected to the amplifier 5 through a cable 6 and also connected to a force (load) measuring member, for example, a load cell 12 in the unit 10 through a cable 12a, and a micro computer 40, that is, a personal computer connected to the data recorder 30 through a cable 7.

As shown in FIG. 2, the calibration unit 10 comprises a bottom frame 11, the load cell 12, the laser displacement meter 13, a force(load) transmitting portion 14 as a holding case of the laser displacement meter 13, supporting pillars 16, a preload member or the like. The preload member comprises, for example, a clamping screw 18, a plate-like member 19, arms 21, an axis 22 or the like. The bottom frame 11 is attached to a mounting portion for anvil of the tester 1 by a mounting screw 2 for anvil. On an inner and bottom surface of the bottom frame 11, the load cell 12 is attached exchangeably. The load cell 12 is for continuously measuring forces which are applied thereto.

In four positions of an upper surface of the bottom frame 11, the supporting pillars 16 are mounted, which comprise rollers 15 which guide movably up and down the force transmitting portion 14. The laser displacement meter 13 is disposed in the force transmitting portion 14 with holding through protecting members 14a. The laser displacement meter 13 is for continuously measuring distances between the fixed point at the laser displacement meter 13 and a point at the force transmitting portion 14.

A projecting portion 14b of the force transmitting portion 14 is attached thereto so that a bottom surface of the projecting portion 14b may be brought into contact with an upper surface of the load cell 12.

Four supporting pillars 16 are mounted to the bottom frame 11 and a receiving plate 17 is mounted to one supporting pillar 16a with projecting. A screw portion of the clamping screw 18 is screwed through the receiving plate 17. As shown in FIG. 3, the plate-like member 19 is mounted to an upper end portion of the clamping screw 18 by a bolt 23 and the arms 21 are attached to right and left of the plate-like member 19.

Each inner end portion in a side of the force transmitting portion 14, of the arms 21 are connected pivotally on a rotation axis 14c which is attached to an upper end portion of the force transmitting portion 14. Each portion of the inner end portion of the arms 21, which is slightly near the plate-like member 19 is rotatably connected to the supporting pillars 16 by the axis 22.

When the arms 21 are pitched with fulcrum of axis 22, the force transmitting portion 14 is guided by the rollers 15 to move up and down with not changing the direction thereof.

When a knob 18a of the clamping screw 18 is operated from a state that the clamping screw 18 is loosened, as shown in FIG. 5 to clamp the clamping screw 18 to make it in a state that it is clamped, as shown in FIG. 4, the force transmitting portion 14 is moved to downwardly, thereby, it is possible to apply a predefined force to the load cell 12 through the force transmitting portion 14. After set in this state, the calibration unit 10 is installed to the tester 1.

That is, the bottom frame 11 of the calibration unit 10 is mounted to the mounting portion for anvil of the tester 1 by the mounting screw 2 for anvil and a dummy indenter 20 attached to project to a top of the force transmitting portion 14 is inserted into a mounting hole for indenter of the tester 1. Then, the installation of the calibration unit 10 to the tester 1 is completed.

Accordingly, because the load cell 12 is pressed by the force transmitting portion 14 by operating the preload member, it is possible to mount the calibration unit 10 to the tester 1 in the state of applying the predefined force to the load cell 12. The preload member is used as the force removing member when the load cell is exchanged.

As above-described, it is possible to easily install the calibration unit to the mounting portion for anvil of the tester. Further, because the dummy indenter is inserted into the mounting hole for indenter of the tester at the time, it is possible to certainly mount the calibration unit to the tester.

The way of calibration for the hardness tester and evaluation for dynamic characteristic of the load cell will be explained as follows. As shown in FIGS. 1 and 6, signals of measured forces applied to the load cell 12, which are measured by the load cell 12 are continuously input to the computer 40 through the cable 12a, the data recorder 30 and the cable 7. Signals of measured values of the distances between the fixed point of the laser displacement meter 13 and the point of the force transmitting portion 14, which measured by the laser displacement meter 13 are continuously input to the computer 40 from the laser displacement meter 13 through the cable 13, the amplifier 5, the cable 6, the data recorder 30 and the cable 7. In the micro computer 40, a dynamic calculation is executed based on the signals which are obtained by the laser displacement meter 13 and the load cell 12. Reference numeral 50 denotes a containing case for the calibration unit 10.

When the calibration is carried out, as shown in FIG. 7, a preliminary test force 60a, an additional test force 60b, a retention of a total test force 60c, an unloading of the additional test force 60d and the preliminary test force 60e are applied to the load cell 12, in order, similarly in the Rockwell hardness test. Each measured value from the laser displacement meter 13 and the load cell 12 in each step of 60a to 60e is displayed on the display portion 40a of the computer 40.

An example thereof is shown in FIG. 7. A polygonal line 70A shows displacements which are measured by the laser displacement meter 13 and a polygonal line 70B shows test forces which are measured by the load call 12, respectively. The polygonal lines 70A and 70B in FIG. 7 show the case that the calibration is correctly carried out.

When the portion indicated by the arrow P of the polygonal line 70B shown in FIG. 7 has a peak 70p as shown in FIG. 8A and the portion indicated by the arrow Q of the polygonal line 70B shown in FIG. 7 do not has straight line, the calibration is incorrectly carried out.

Each detected signal from the laser displacement meter and the load cell is continuously input to the micro computer, so that the test forces and displacement amounts according to the test forces can be evaluated with changing the test forces by the micro computer, it is possible to carry out the dynamic evaluation of the tester. It is also evaluate the dynamic characteristic of the load cell.

At the same time, the measured value, that is, displacement shown by the displacement gage 4 incorporated in the tester 1 is observed visually and filled in a measurement data chart 41. The measurement of the displacement is to measure a strain, that is, a displacement amount of the load cell 12. That is, as a load cell of the calibration unit 10, the one which can be also used as a displacement gage which has been operated so that a predefined deformation may be caused by applying a predefined force is employed.

Further, the data of the measured values displayed on the display portion 40a of the computer 40 is filled in a measurement data chart 42, so that a static evaluation is carried out by comparing the values filled in both data charts 41 and 42 each other.

When the predefined test force is applied to the load cell, the force and the displacement amount of the load cell according to the test force are calculated by the micro computer, so that it is possible to carry out the static evaluation based on the calculated value.

According to the calibration apparatus for the Rockwell hardness tester in the first embodiment of the present invention, it is possible to carried out the dynamic test in addition to the static test with the tester. Therefore, it is possible to evaluate the dynamic characteristic of the load cell in the first embodiment.

Further, it is possible to detect a forcing speed of the test force, a change of test force during the operation, an overshoot of the test force, which is the peak 70p above-described, or the like. Yet it is possible to detect the progress of the detection of the displacement of the load cell during the operation.

It is possible to carry out the dynamic and static test in a Vickers hardness tester by exchanging the load cell. It is possible to exchange the load cell by loosing the arms 21 with operating the knob 18a, as shown in FIG. 5 and by pulling out the force transmitting portion 14.

The calibration method for a calibration apparatus and for a hardness tester according to the second embodiment will be described as follows. The calibration unit 10 and the calibration apparatus above-described are also used in the second embodiment.

After the calibration unit 10 is installed to the tester 1, as shown in FIG. 1, in the same way as that of the first embodiment, a rating of the load cell 12, that is, a maximum test force which can be measured by the load cell 12 is loaded to the load cell 12. That is, when the rating of the load cell 12 is 2 kN, the test force of 2 kN is applied to the load cell 12. An output power(mV/V) of the load cell 12 in the time is memorized in the data recorder 30.

Then, based on the outputs of the load cell 12 when the rated force, that is, the rating is loaded and when no-load is loaded, a relation between the forces and the outputs is calculated as a linear calibration approximation, as shown in an equation [math 1], by the data analysis software which is installed in the micro computer 40, so that the equation [math 1] is memorized in the micro computer 40. The equation [math 1] shows a characteristic of the calibration apparatus, that is, the load cell 12.

$$y=a_1x+b_1 \quad \text{[math 1]}$$

wherein y is a force(kN), x is an output power(mV/V) of the load cell, a1 is a constant, and $b_1$ is an offset.

Figure 9:
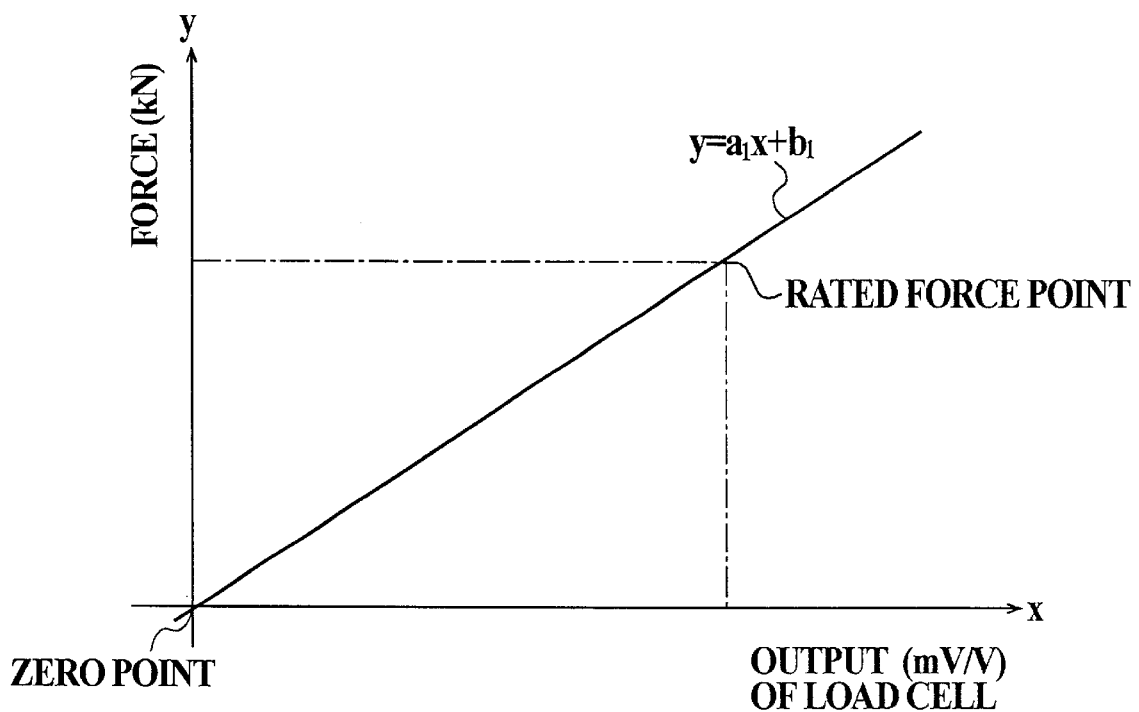
FIG. 9 is a graph showing the principle of a calibration according to the second embodiment of the invention.

This is shown in FIG. 9. Then, the calibration of another hardness tester will be carried out by using the calibration apparatus having the load cell which has the characteristic obtained as above-described.

To an other tester to be calibrated, the calibration unit 10 is installed to the tester, the portion of which is obtained by removing the anvil and indenter from the tester.

After the calibration unit 10 is installed to the tester, the tester is operated in the same way as hardness test, a test force of n(kN) is applied to the load cell 12. The test force of n(kN) is displayed on the display portion 40a. The output power, that is, a voltage of the load cell 12 in the time is memorized in the data recorder 30. An actual force, that is, an actual test force of M(kN) working to the tester is calculated according to the output power and the equation [math 1] by the computer 40, and a function of n=f(M) is calculated. This is the characteristic of the tester. The function of n=f(M) is input in the micro computer 40.

Figure 10:
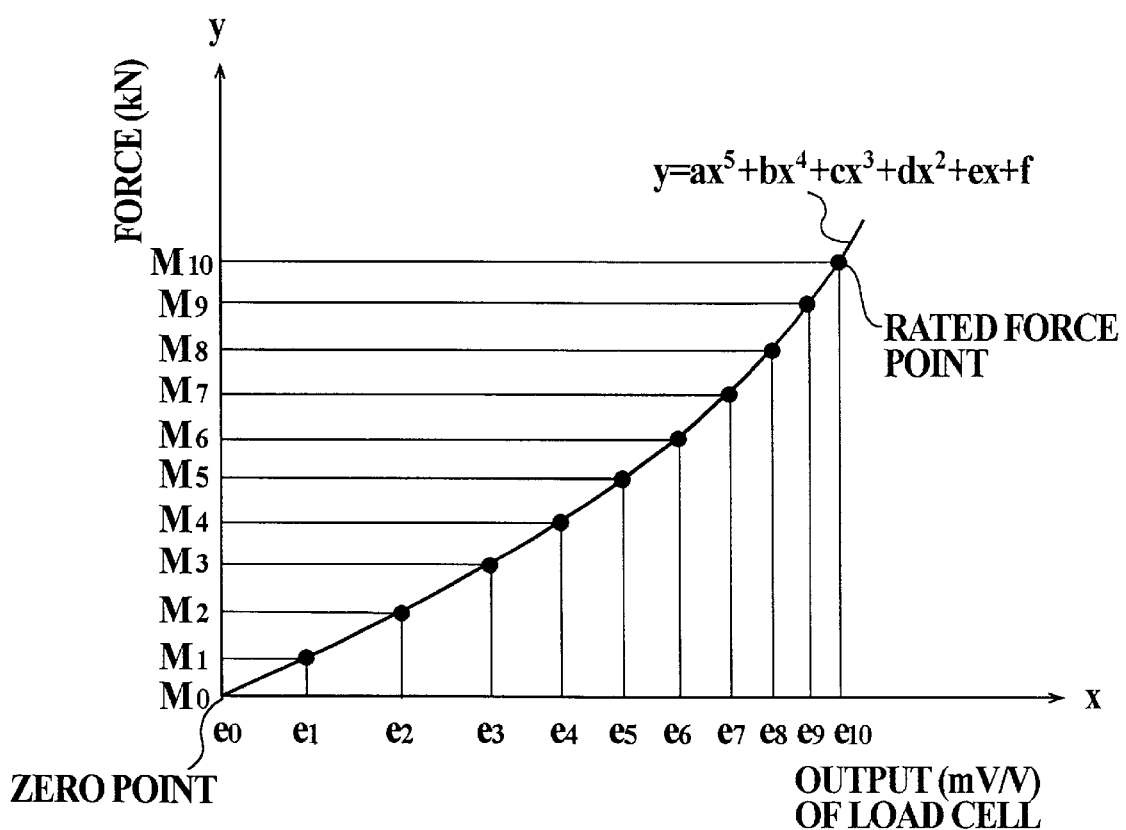
FIG. 10 is a graph showing the principle of a calibration according to the third embodiment of the invention.
Figure 11:
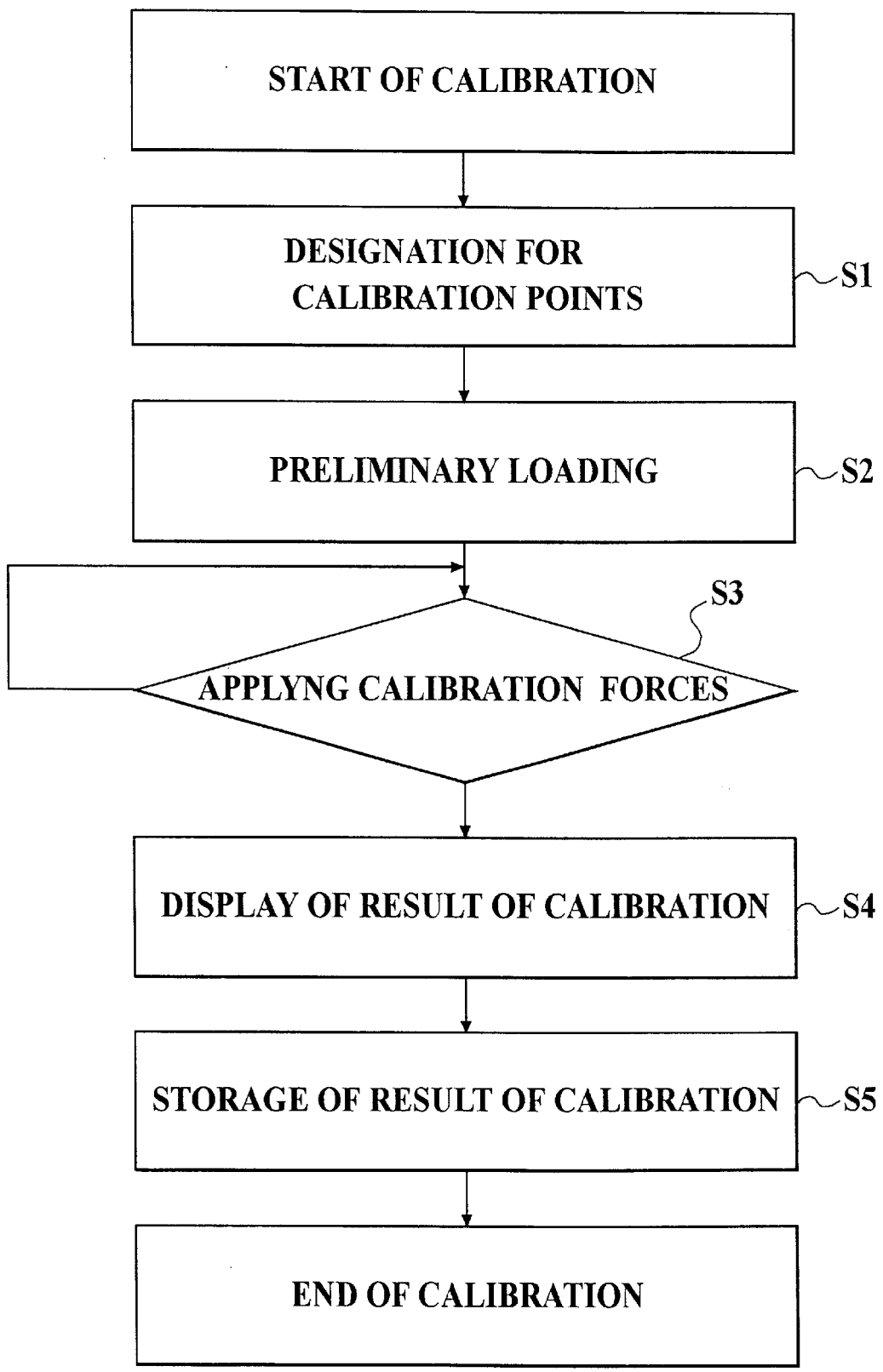
FIG. 11 is a flow chart showing the steps of the calibration of FIG. 10.

Another calibration method for a calibration apparatus and for a hardness tester according to the third embodiment will be described as follows. FIG. 10 is a graph showing the principle of the calibration, and FIG. 11 is a flow chart showing the steps of the calibration. The calibration unit 10 and the calibration apparatus in the first embodiment are also used in the third embodiment.

In the third embodiment, the calibration for the load cell 12 which is mounted to the calibration unit 10 of the calibration apparatus shown in FIG. 1, that is, the calibration for the calibration apparatus is carried out as follows.

The calibration unit 10 is installed to the tester 1, the portion of which is obtained by removing the anvil and indenter from the tester 1, in the same way as the first embodiment.

Then, test forces are applied to the load cell 12 of the tester 1. In the third embodiment, as shown in FIG. 10, a rating force of $M_{max}$(kN) is divided into ten forces of $M_0$, $M_1$, $M_2$, $M_3$, ..., and $M_{10}$(=$M_{max}$kN), which have the same intervals between them, and the forces as the test forces are applied to the load cell 12 in order. Each output power $e_1$, $e_2$, $e_3$, ..., $e_{10}$ (mV/V) of the load cell 12 according to the test forces is input in the micro computer 40 through the data recorder 30. A relation between the test forces of M(kN) and the outputs of the load cell are calculated as a multidimensional calibration approximation, as shown in an equation [math 2], by the data analysis software which is installed in the micro computer 40, so that the equation [math 2] is memorized in the micro computer 40. The equation [math 2] shows a characteristic of the load cell 12.

$$y=ax^5+bx^4+cx^3+dx^2+ex+f \quad \text{[math 2]}$$

wherein y is a test force(kN), x is an output power(mV/V) of the load cell, a, b, c, d, and e are constants, and f is an offset.

Next, the calibration process for the load cell is shown in the flow chart as shown in FIG. 11.

In a step S1, a designation for the calibration points, that is, the division of the rated force into the ten points with the same Intervals is carried out. In a step S2, a preparation of calibration, that is, a preliminary loading is carried out by applying the no-load and the rated force to the load cell 12 for three times, respectively. The preliminary loading is for stabilizing the outputs of the load cell.

In a step S3, after the preliminary loading is completed, the test forces of the no-load $M_0$ to the rated force $M_{10}$ are orderly applied to the load cell 12 and each output power of the load cell 12 according to each calibration point is measured and input to the micro computer 40. The step S3 is carried out for several times. The minimum for the step S3 is three times to proceed to a next step. In the step S3, the measurement is carried out by shifting a position of the tester 1 in direction of rotation. For example, when the step S3 is repeated for three times, the position of the tester 1 is shifted 120°, respectively. The maximum for the step S3 is five times, which is enough to calibrate.

Thereafter, in a step S4, for calculating a calibration approximation, average values of the data obtained in the step S3 are determined in each calibration point. Then, a multidimensional calibration approximation is calculated in the micro computer 40 as a result of the calibration and displayed on the display portion 40a. In a step S5, the multidimensional calibration approximation is memorized and stored in the data analysis software in the micro computer 40. Then, the calibration for the load cell 12 is completed.

The calibration for the commercial hardness tester is performed in the same way as the second embodiment by employing the calibration apparatus of which load cell is calibrated as above-described.

After the calibration unit 10 is installed to the commercial hardness tester, the tester is operated in the same way as the hardness test, test forces of ni including no-load are applied to the load cell 12. The test forces of $n_i$ are displayed on the display portion 40a. The outputs of the load cell 12 in the time are memorized in the computer 40. The actual test forces of M. working to the tester are calculated according to the outputs(mV/V) of the load cell 12 and the equation [math 2] by the computer 40, and a function of $n_i$=f($M_i$) is calculated. This is the characteristic of the tester to be calibrated. The function of $n_1$=f($M_1$) is input in the micro computer 40.

As above-described, it is possible to easily install the calibration unit to the commercial hardness tester, so that it is possible to calibrate the calibration apparatus and the hardness tester in the same way as that of the ordinary hardness test.

According to the calibration apparatus which is calibrated in the calibration method of the third embodiment, because it is made that the calibration points are a number of points, it is possible to carry out the dynamic measurement in the hardness tester in addition to the static measurement.

Further, because it is made that the calibration points are a number of points, it is possible to minimally restrain the hysteresis of the load cell and error by repeating with the dynamic test.

It is possible to carry out the dynamic and static tests in a Vickers hardness tester by exchanging the load cell of the calibration apparatus. It is possible to change the load cell by loosing the arms 21 with operating the knob 18a, as shown in FIG. 5 and by pulling out the force transmitting portion 14.

Referring now to FIGS. 12 to 19, an apparatus for evaluating a dynamic characteristic of a specimen according to the fourth embodiment of the present invention will be described as follows.

Figure 12:
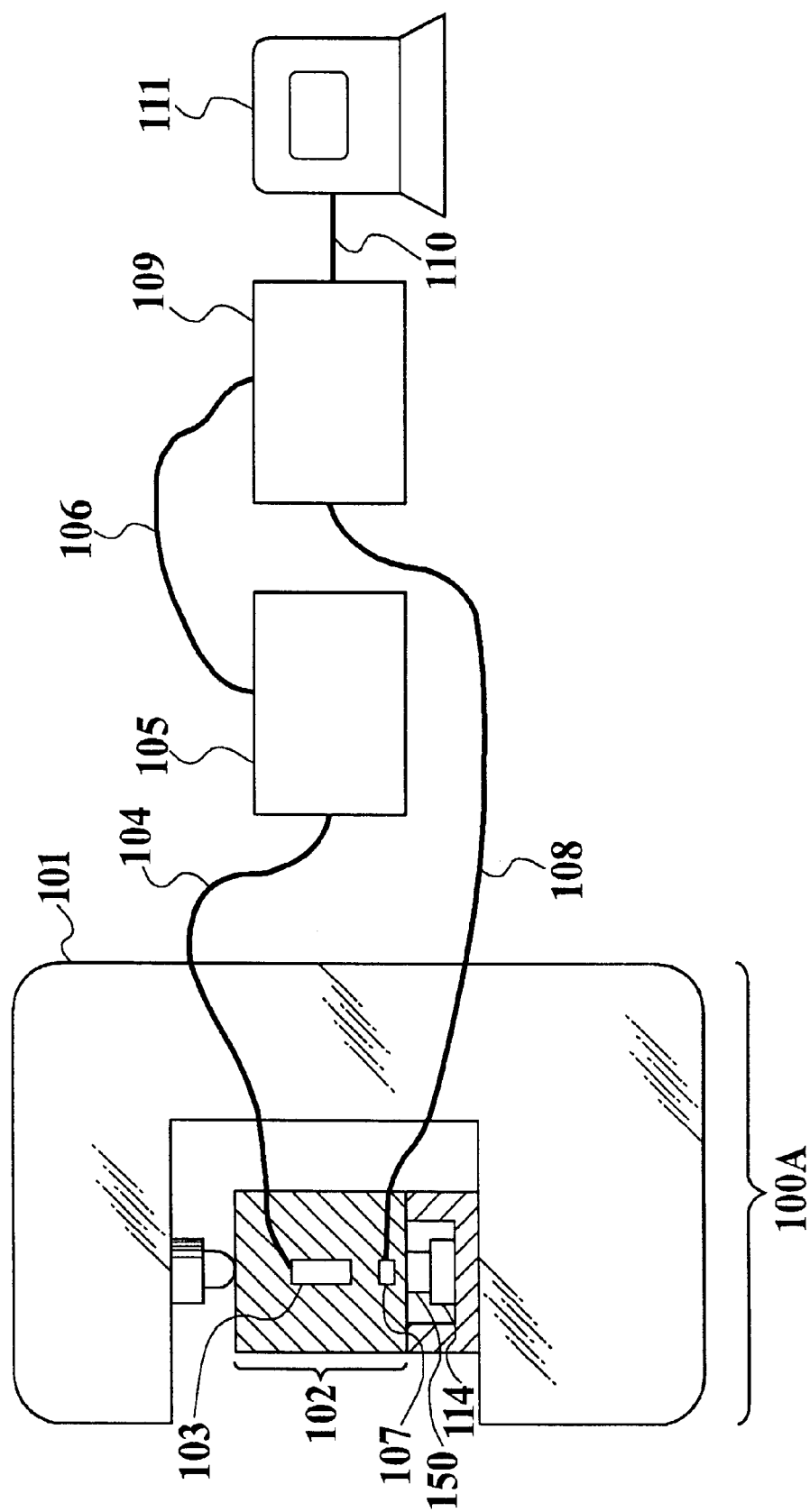
FIG. 12 is a schematic illustration of whole constitution of an apparatus for evaluating a dynamic characteristic of a specimen according to the fourth embodiment of the present invention.
Figure 13:
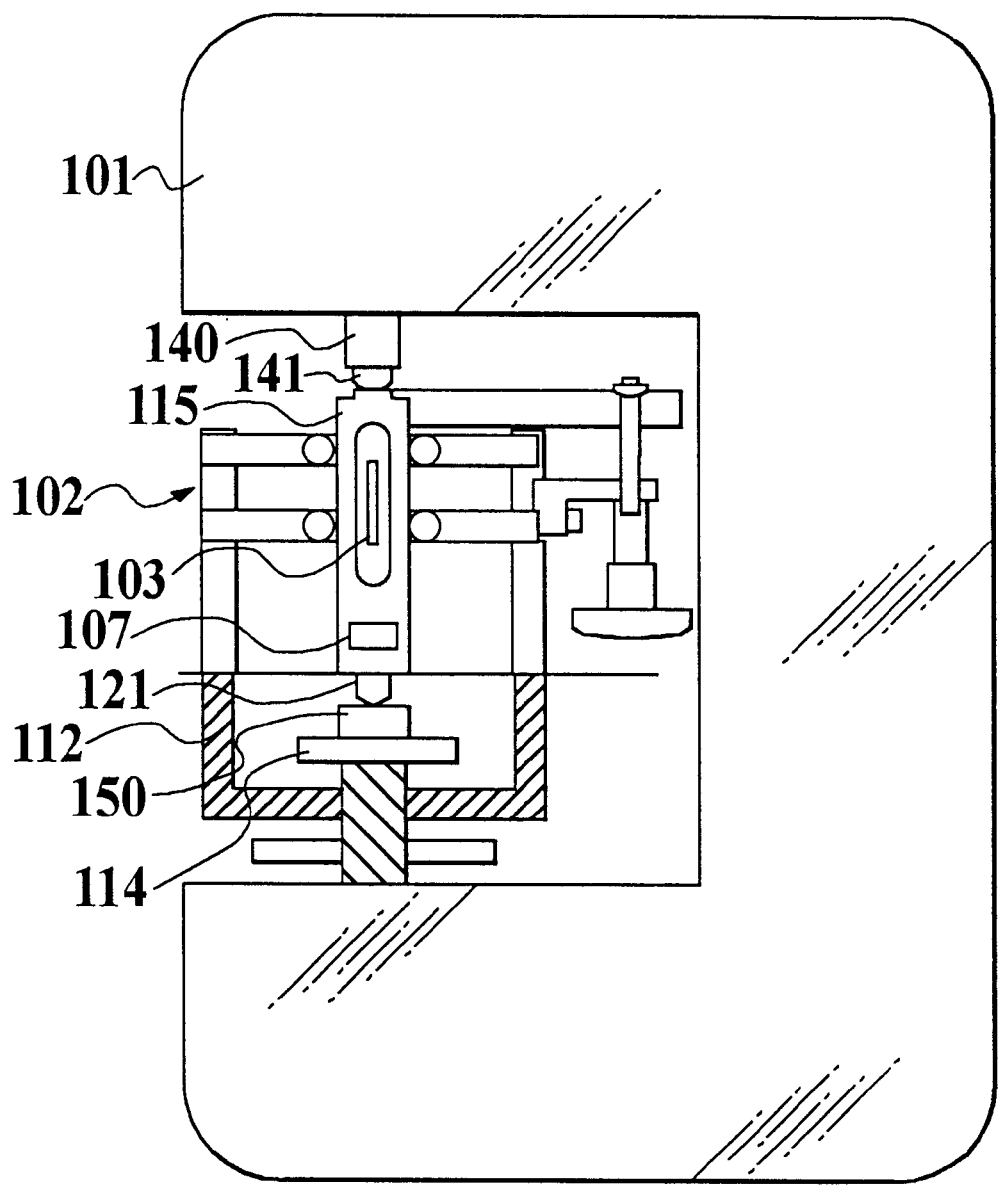
FIG. 13 is an enlarged front view of a portion 100A of FIG. 12.
Figure 14:
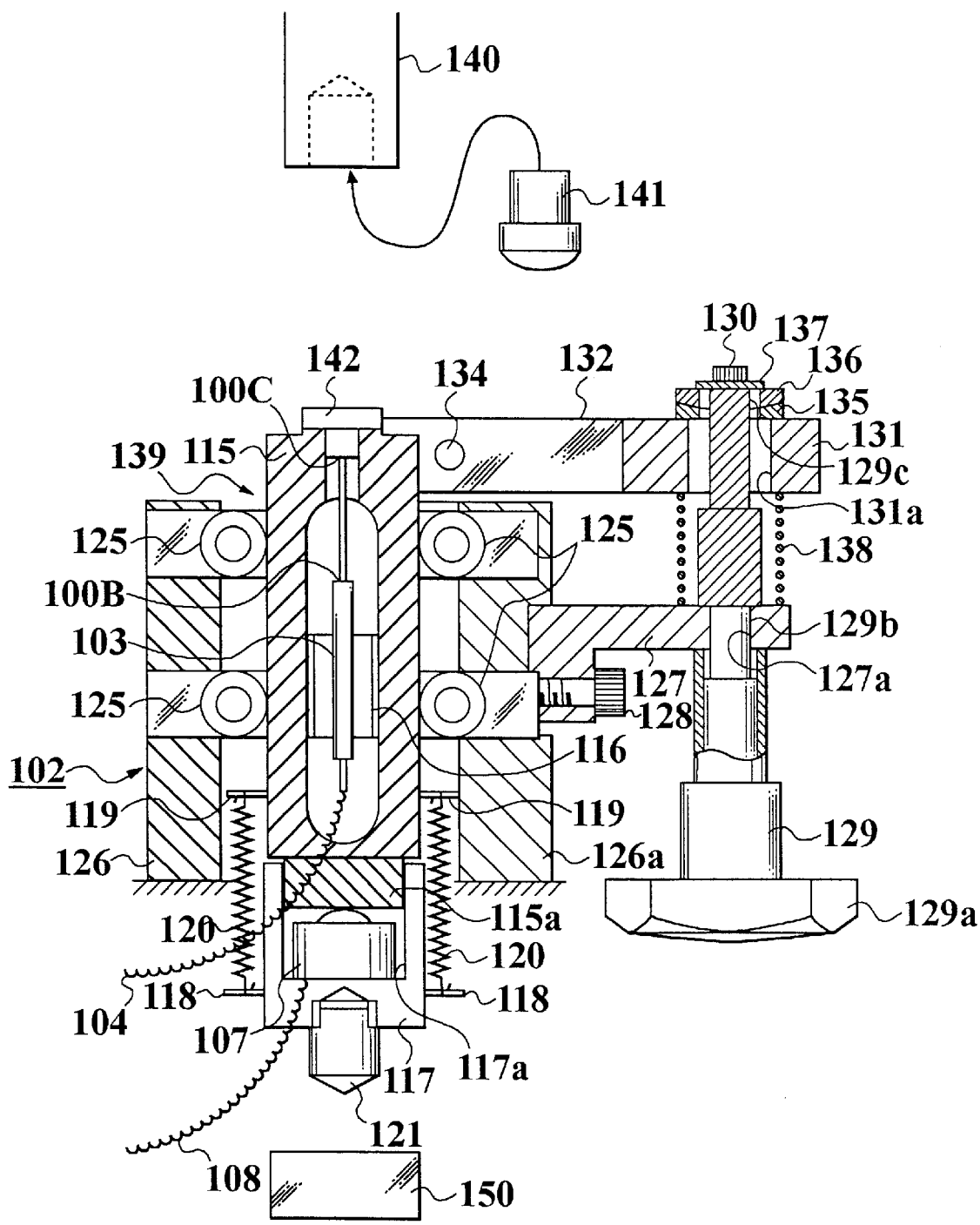
FIG. 14 is an enlarged front view, partly in section, showing a main portion of FIG. 13.
Figure 15:
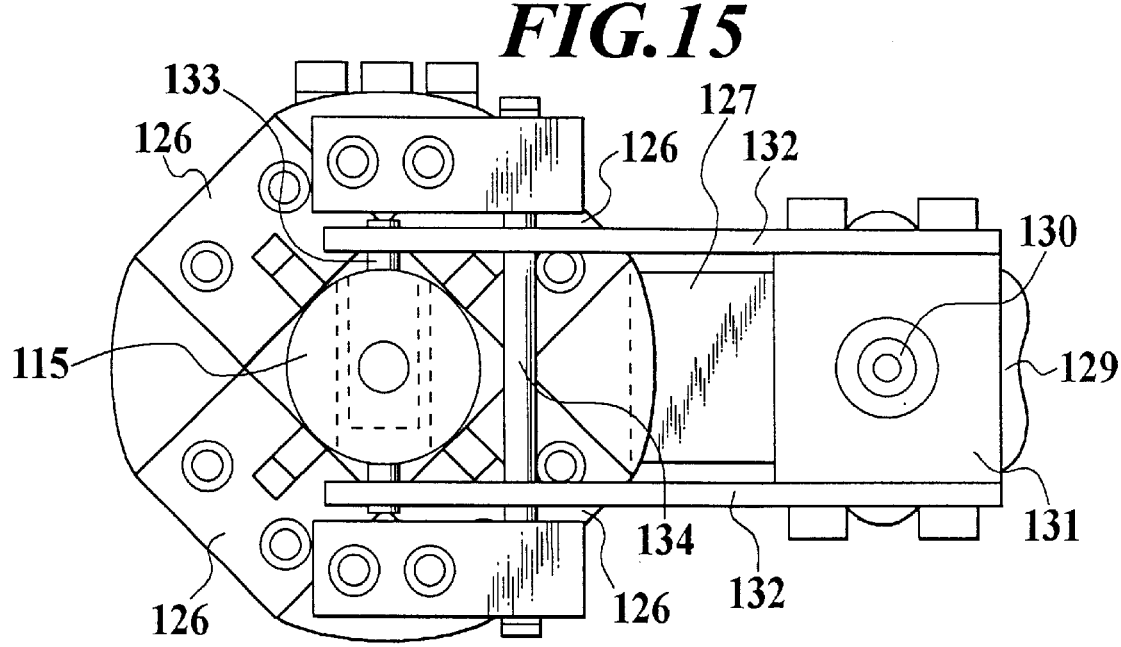
FIG. 15 is a plan view showing the main portion of FIG. 13.
Figure 16:
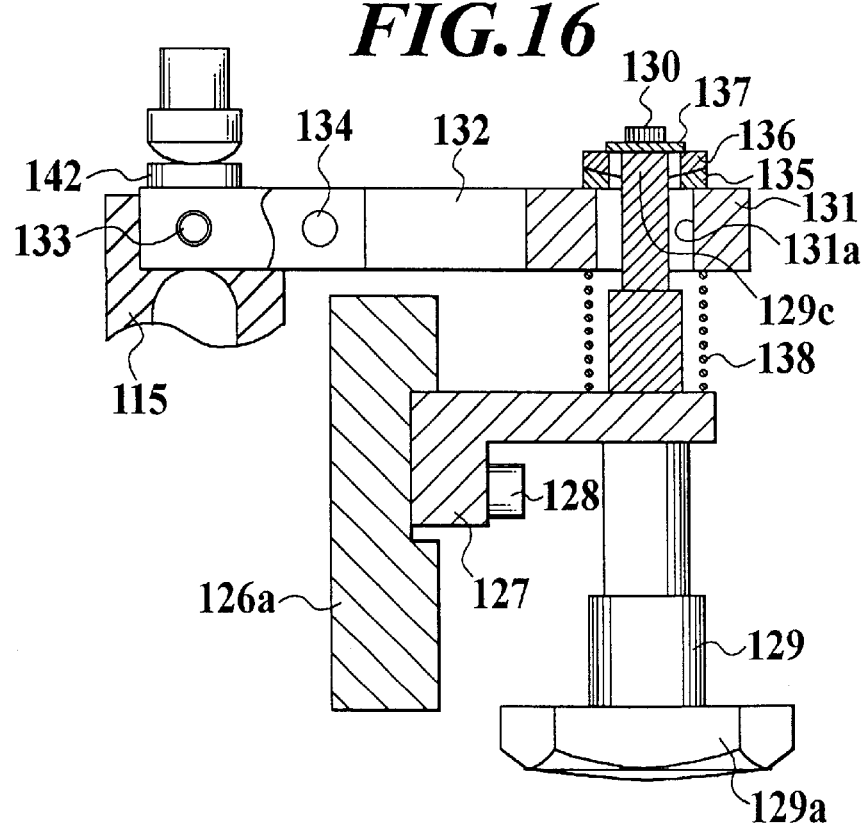
FIG. 16 is a partial front view, partly in section, of FIG. 14, for explaining an operation thereof.
Figure 17:
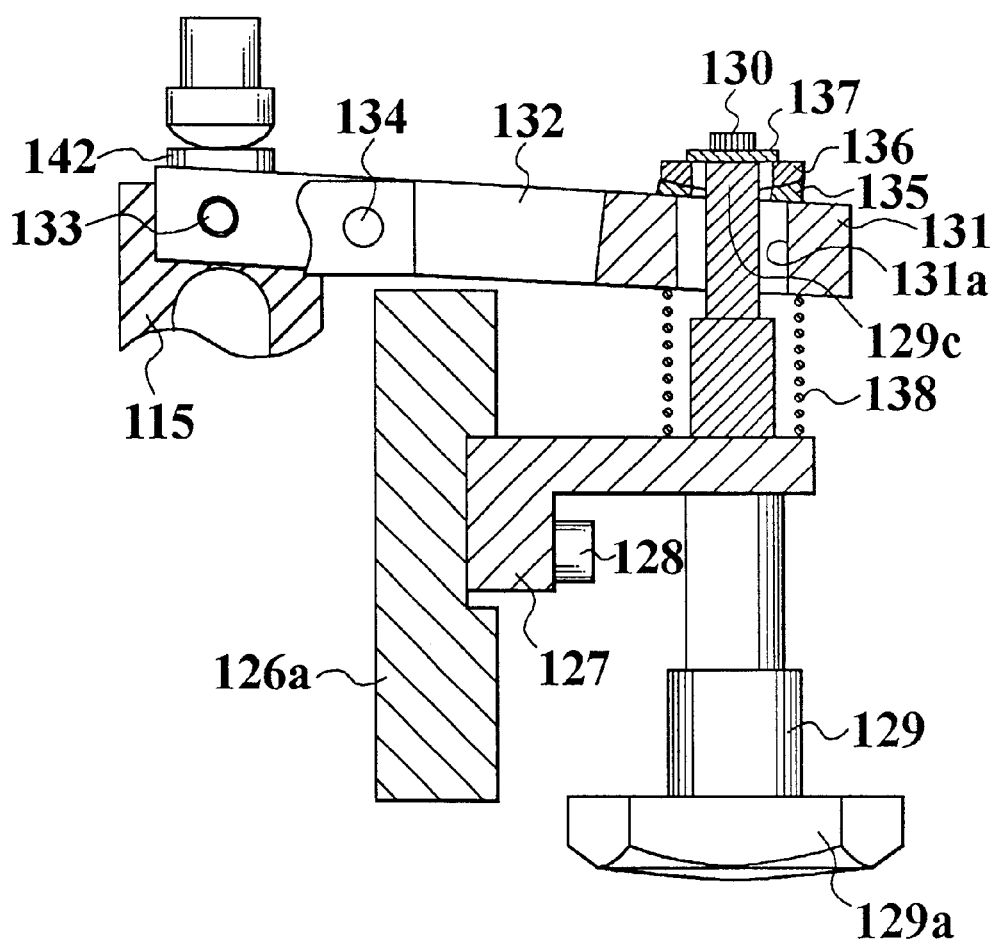
FIG. 17 is a partial front view, partly in section, of FIG. 14, for explaining an operation thereof.
Figure 18:
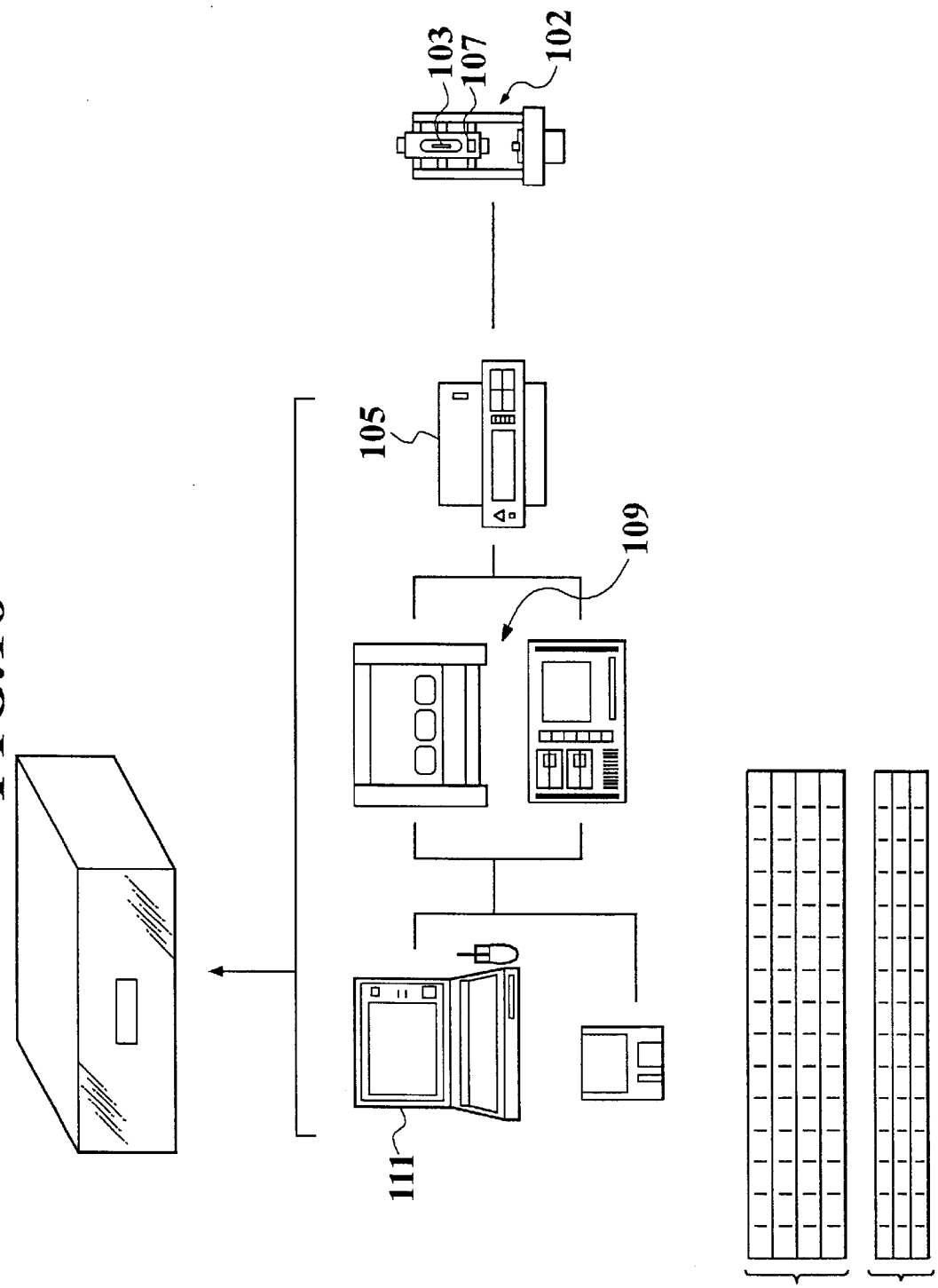
FIG. 18 is a schematic illustration explaining the dynamic characteristic evaluation by the apparatus for evaluating a dynamic characteristic of a specimen according to the fourth embodiment of the present invention.
Figure 19:
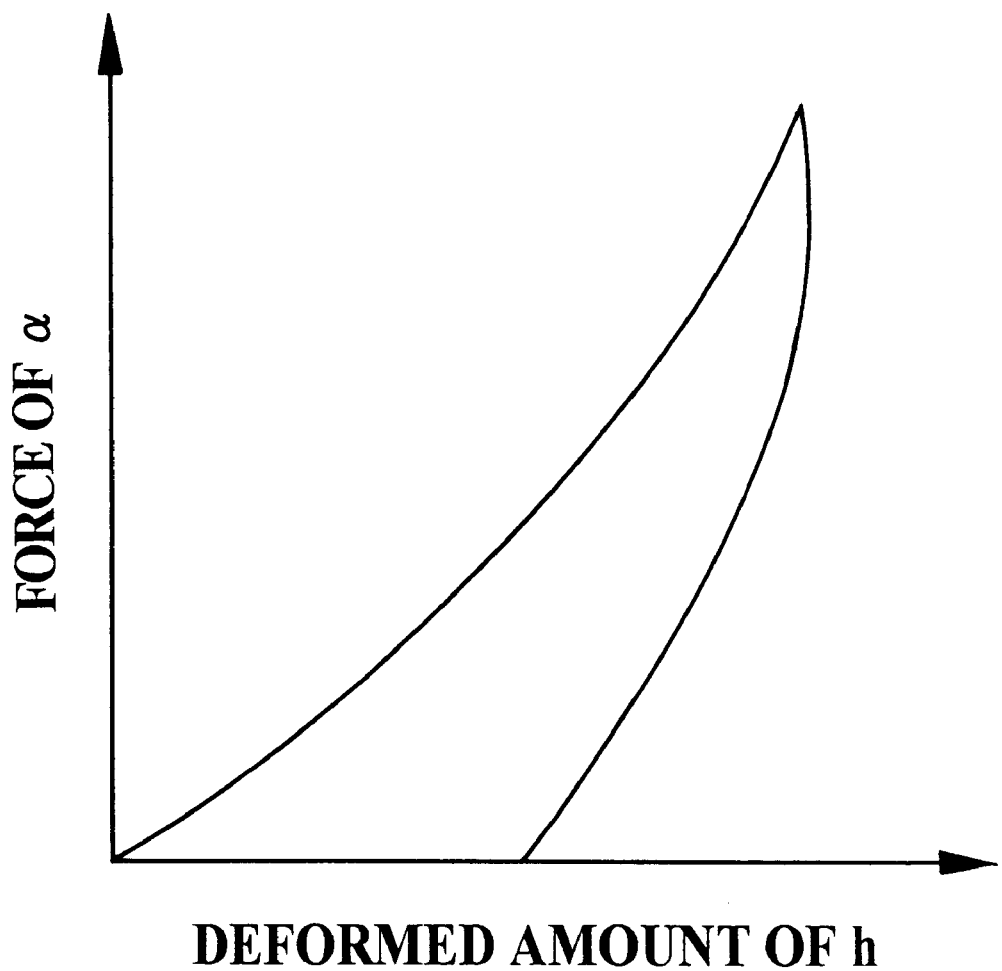
FIG. 19 is a graphical representation showing a dynamic characteristic of a specimen according to the fourth embodiment.
Figure 20:
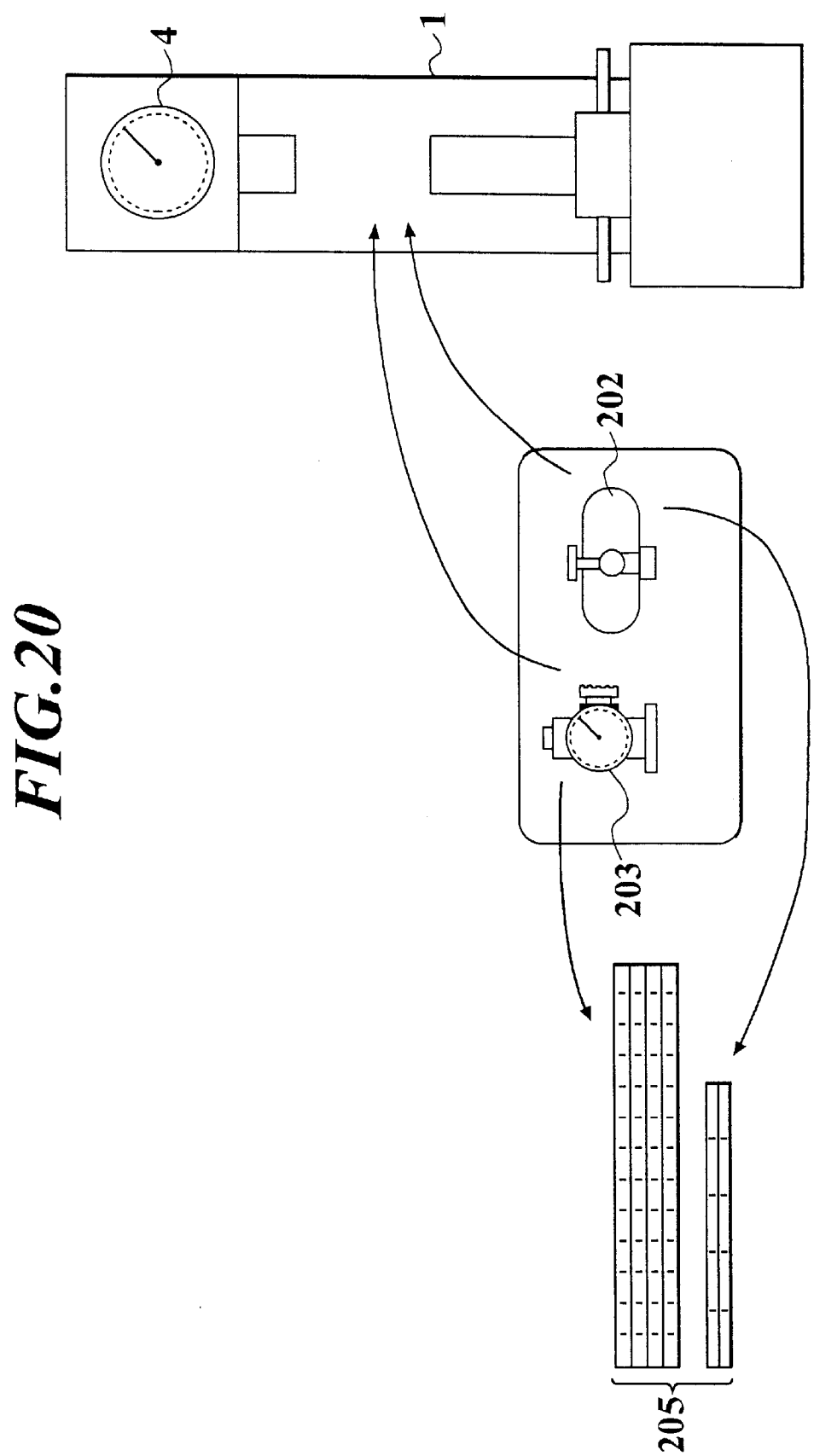
FIG. 20 is a schematic view showing a prior calibration apparatus.

FIG. 12 is a schematic illustration of whole constitution of the apparatus for evaluating a dynamic characteristic of a specimen according to the fourth embodiment of the present invention, FIG. 13 is an enlarged front view of a portion 100A of FIG. 12, FIG. 14 is an enlarged front view, partly In section, showing a main portion of FIG. 13, FIG. 15 is a plan view showing the main portion of FIG. 13, FIGS. 16 and 17 are partial front views, partly in section, of FIG. 14, for explaining an operation thereof, FIG. 18 is a schematic illustration explaining the evaluation for a dynamic characteristic of a specimen by the apparatus for evaluating a dynamic characteristic of a specimen according to the fourth embodiment of the present invention, FIG. 19 is a graphical representation showing a dynamic characteristic of a specimen according to the fourth embodiment.

As shown in FIG. 12, the apparatus for evaluating a dynamic characteristic of a specimen according to the fourth embodiment, the apparatus comprises, for example, a hardness tester 101, a unit 102 installed thereto, an amplifier 105 connected to a distance measuring member, for example, a laser displacement meter 103 or the like through a cable 104, a data recorder 109 connected to the amplifier 105 through a cable 106 and to a load cell 107 as a force(load) measuring member in the unit 102 through a cable 108, a computer 111 connected to the data recorder 109 through a cable 110, or the like.

As shown in FIG. 14, the unit 102 comprises a movable portion 139 which is movable up and down, comprising a force(load) transmitting portion 115, the load cell 107, an indenter 121 or the like: rollers 125 for guiding the movable portion 139: supporting pillars 126 to which the rollers 125 are attached: a position adjusting member comprising, for example, a receiving plate 127, a clamping screw 129, a plate-like member 131, arm portions 132, axes 133 and 134, a concave spherical washer 135, a convex spherical washer 136: or the like.

As shown in FIG. 14, the laser displacement meter 103 is disposed in the force transmitting portion 115 of the movable portion 139 through a protecting member 116. Positions in the vertical direction of the laser displacement meter 103 and the protecting member 116 are fixed so as not to move. The force transmitting portion 115 can be moved up and down around the protecting member 116 around the laser displacement meter 103.

The force transmitting portion 115 has, for example, a housing having a cylindrical shape. As shown in FIG. 15, a back surface side of the force transmitting portion 115 has an opening portion therethrough the laser displacement meter 103 can be installed and removed.

The laser displacement meter 103 is for continuously measuring distances from the fixed point 100B at the laser displacement meter 103 to a point in the force transmitting portion 115, for example, a point 100C at a lower surface of a force(load) receiving portion 142 of the force transmitting portion 115.

A holder 117 has, for example, a concave portion 117a opening to an upper portion and approximately U-shape in cross section. In the concave portion 117a of the holder 117, the load cell 107 is disposed. The concave portion 117a has a size which is the same as or slightly larger than that of a convex portion 115a on a lower portion of the force transmitting portion 115, so that it is possible to insert the convex portion 115a in the concave portion 117a.

On side portions of the holder 117, holding portions 118 are disposed to project to outer sides and on lower side portions of the force transmitting portion 115, holding portions 119 are disposed to project to outer sides. A helical coil spring 120 as energising member is hooked to the holding portions 118 and 119 to bridge them in a state of having tension. Thereby, the holder 117 and the load cell 107 are energised to a side of the force transmitting portion 115 in the state that the convex portion 115a on the lower portion of the force transmitting portion 115 is inserted in the vicinity of an upper peripheral portion of the concave portion 117a of the holder 117 so that it may be maintained the state that an upper end portion of the load cell 107 is contacted with a lower end surface of the force transmitting portion 115. Accordingly, when the force is applied to the load cell 107 thereby a length of the load cell 107 in the vertical direction becomes slightly short, the helical coil spring 120 slightly shortens and the concave portion 117a of the holder 117 moves slightly in the upper direction against the convex portion 115a of the force transmitting portion 115. Therefore, the upper end portion of the load cell 107 is always contacted to the lower end surface of the force transmitting portion 115.

When the holder 117 is moved in a direction of moving far away from the force transmitting portion 115 against the energising force of the helical coil spring 120, it is possible to make a space between the load cell 107 and the force transmitting portion 115, so that it is possible to exchange the load cell 107.

According to the apparatus of the invention, because the holder is energised against the force transmitting portion by the energising member, it is possible to make the force measuring member held in the holder contact to the force transmitting portion. Further, even if the force measuring member is deformed by being applied the force, it is possible to energise the holder and the force measuring member against the force transmitting portion by the energising member with the deformation of the force measuring member. Therefore, it is possible to always make the force measuring member contact to the force transmitting portion.

In a bottom portion of the holder 117, the indenter 121 is attached detachably. A lower end portion of the indenter 121 has, for example, a pyramidal shape. When the lower end portion of the indenter 121, for example, the top of the pyramidal shape is pressed to a specimen 150, the specimen 150 is deformed.

A force(load) applying member 140 described later of the hardness tester 101, a dummy indenter 141 described later, the force transmitting portion 115, the holder 117, and the indenter 121, have larger hardness compared to the load cell 107 and the specimen 150. Accordingly, when a force is applied from the force applying member 140 to the force receiving portion 142 of the force transmitting portion 115, it is assumed that only the load cell 107 and the specimen 150 are deformed by the force. It is also assumed that a force applied to the load cell 107 is the same as that of the specimen 150.

Therefore, when forces of β applied to the load cell 107 is continuously determined, it is possible to continuously determine forces of α which are applied to the specimen 150. In the peripheries of the force transmitting portion 115, a plurality of supporting pillars 126 are disposed, to which a plurality of rollers 125 which guide movably up and down the force transmitting portion 115 are attached rotatably. Each bottom portion of the supporting pillars 126 is mounted and fixed to mounted portions 112 of the hardness tester 101. The receiving plate 127 projecting in the horizontal direction is fixed to one supporting pillar 126a among the supporting pillars 126, for example, by a bolt 128.

To a male screw portion 127a of the receiving plate 127, a screw portion 129b of the clamping screw 129 is screwed. As shown in FIGS. 16 and 17, a through hole 131a for penetrating a shaft portion 129c of the clamping screw 129 is formed in the plate-like member 131. On an upper surface of the plate-like member 131, the concave spherical washer 135 is fixed so that the concave surface side thereof may face to the upper side and not stop up or cover the through hole 131a. The convex spherical washer 136 is disposed on the concave surface of the concave spherical washer 135 so that a convex surface side thereof may fit to the concave surface side of the concave spherical washer 135. Then, the convex spherical washer 136 is rotatably moved against the concave spherical washer 135.

A bolt 130 is clamped to an upper end portion of the shaft portion 129c of the clamping screw 129 in a state of inserting the upper end portion of the shaft portion 129c to the through hole 131a of the plate-like member 131, a through hole 135a of the concave spherical washer 135, a through hole 136a of the convex spherical washer 136 and a washer 137. Then, the washer 137 and the bolt 130 are secured to an upper end portion of the shaft portion 129c. The washer 137 has an outside diameter which is larger than that of the through hole 136a of the convex spherical washer 136, so that the upper end portion of the shaft portion 129c of the clamping screw 129 does not slip off in a lower direction. Further, a compression coil spring 138 having a compression force is disposed around the shaft portion 129c of the clamping screw 129, so that the plate-like member 131 is energised in the upper direction by the compression coil spring 138.

Accordingly, as shown in FIGS. 16 and 17, the plate-like member 131 is smoothly pitched because the each concave and convex surface of the spherical washers 135 and 136 becomes sliding surface.

Each through hole 131a and 135a has an inside diameter which is larger than an outside diameter of the shaft portion 129c so that the shaft portion 129c may not contact to the through holes 131a and 135a when the plate-like member 131 and the concave spherical washer 135 are moved around the shaft portion 129c of the clamping screw 129 with the arm portions 132.

As shown in FIGS. 16 and 17, each one end of the arm portions 132 is rotatably connected to each other by the axis 133 which is disposed in the upper end portion of the force transmitting portion 115. Each portion of the arm portions 132, which is slightly near the plate-like member 129 compared to the one end is rotatably connected to each other to the supporting pillars 126 by the axis 134.

When the arm portions 132 are pitched with fulcrum of axis 134, the movable portion 139 which comprises the force transmitting portion 115, the holder 117, the load cell 107 in the holder 117, the indenter 121 attached to the bottom portion of the holder 117 or the like is guided as a whole by the rollers 125 attached to the supporting pillars 126 to move up and down with not changing the direction.

When a knob 129a of the clamping screw 129 is screwed to make a distance between the receiving plate 127 and the plate-like member 131 short, the screw portion 129b of the clamping screw 129 is moved in the lower direction of the receiving plate 127. Then, the arm portions 132 are pitched with fulcrum of axis 134, so that the movable portion 139 is moved in the upper direction with being guided by the rollers 125. Contrary, when the knob 129a of the clamping screw 129 is screwed to make a distance between the receiving plate 127 and the plate-like member 131 long, the screw portion 129b of the clamping screw 129 is moved in the upper direction of the receiving plate 127. Then, the arm portions 132 are pitched with fulcrum of axis 134, so that the movable portion 139 is moved in the lower direction with being guided by the rollers 125.

The force applying member 140 of the hardness tester 101 is provided with the dummy indenter 141. A lower end portion of the dummy indenter 141 has, for example, a hemispherical shape. The force transmitting portion 115 comprises the force receiving portion 142 on the upper end portion thereof to receive a force from the dummy indenter 141 of the force applying member 140. An upper surface of the force receiving portion 142 has a recess surface to suitably receive the dummy indenter 141.

The measured values of the distances of D between the fixed point of the laser displacement meter 103 and the point of the force transmitting portion 115, which measured by the laser displacement meter 103 are continuously input to the computer 111 from the laser displacement meter 103 through the cable 104, the amplifier 105, the cable 106, the data recorder 109 and the cable 110. The computer 111 is programmed to calculate the variations of $\Delta D$ of the distances of D by determining a variation from the initial value.

The measured values of the forces of $\beta$ applied to the load cell 107, which measured by the load cell 107 are continuously input to the computer 111 from the load cell 107 through the cable 108, the data recorder 109 and the cable 110.

The dynamic characteristic of the load cell 107 is evaluated and a deformed amount of h' of the load cell 107 is accumulated as a data, for example, in the computer 111.

The measuring of the deformed amount of h' of the load cell 107 is carried out, for example, by using an indenter in place of the indenter 121, not shown, having a plane surface which is contacted to the specimen table 114 and in a state of removing the specimen 150. In this state, when a force is applied to the force transmitting portion 115 by the hardness tester 101, the variations of the distances of D between the fixed point of the laser displacement meter 103 and the point of the force transmitting portion 115 are continuously measured. At this time, it is assumed that only the load cell 107 is deformed, the measured values are regarded as the deformed amounts of h' of the load cell 107, which are continuously measured in the acting direction.

Then, the dynamic characteristic of the load cell 107 can be evaluated by a relation between the deformed amounts of h' of the load cell 107 and the forces applied to the load cell 107, which are continuously measured respectively.

The computer 111 is programmed to determine the deformed amounts of h by subtracting the deformed amounts of h' from the variations of $\Delta D$ and also programmed to draw up a graph showing a relation between the forces of $\alpha$, that is, the forces of $\beta$ and the deformed amounts of h, for example, as shown in FIG. 19.

Accordingly, by applying the force to the force transmitting portion from the force applying member of the hardness tester, subsequently applying the force to the specimen through the indenter, it is possible to determine the relation between the forces of $\alpha$ applied to the specimen when the specimen is gradually deformed and the deformed amounts of h of the specimen according to the forces of $\alpha$. Therefore, it is possible to carry out the evaluation of the dynamic characteristic of the specimen.

Further, according to the apparatus, the distance of D between the fixed point of the laser displacement meter and the point of the force transmitting portion can be gradually changed. It is possible to determine the variations of ΔD of the distance of D by continuously measuring the distance. The variations of ΔD are the same values as a length of the sum of the deformed amounts of h of the specimen and the deformed amounts of h' of the load cell, so that it is possible to continuously determine the deformed amounts of h of the specimen by subtracting the deformed amounts of h' from the variations of ΔD.

Yet, it is possible to draw up the graph showing the relation between the forces of α applied to the specimen and the deformed amounts of h of the specimen.

A way of evaluation for a dynamic characteristic of a specimen by applying the apparatus for evaluating a dynamic characteristic of a specimen according to the fourth embodiment of the invention will be described In detail as follows.

At first, the specimen 150 will be placed on the specimen table 114. Therefor, as shown in FIG. 17. the knob 129a of the clamping screw 129 is screwed to move the other end portions of the arm portions 132 in a side of the receiving plate 127, that is, the right end of the arm portions 132 in the figure are moved in the lower direction and the movable portion 139 is moved in the upper direction, so that a distance between the indenter 121 and the specimen table 114 is larger than a height of the specimen 150. Thereafter, the specimen 150 is placed on the specimen table 114. Then, the knob 129a of the clamping screw 129 is contrary screwed to move the right end portions of the arm portions 132 in a direction of separating from the receiving plate 127 and the movable portion 139 is moved in the lower direction, so that the top end portion of the indenter 121 is brought into contact with the upper surface of the specimen 150. Further, the knob 129a is further screwed with a little play.

In this state, a force according to a weight of the movable portion 139 is applied to the specimen 150 through the indenter 121 and also applied to the load cell 107. An initial value of $\alpha_0$, that is, $\beta_0$ of the force is required to compensate.

Next, the hardness tester 101 is operated to apply a predefined force to the force receiving portion 142 of the force transmitting portion 115 of the movable portion 139 from the dummy indenter 141 of the force applying member 140. Then, the force of α is applied to the specimen 150 from the indenter 121 disposed in the lower portion of the force transmitting portion 115. At this time, the specimen 150 is gradually deformed by the indenter 121, thereafter, the deformation is saturated to become stable. It is possible to move the movable portion 139 as a whole, so that it is possible to gradually move the movable portion 139 in the acting direction of the force with deformation caused in the load cell 107 and the specimen 150. Because the holder 117 and the load cell 107 are energised to the force transmitting portion 115 by the helical coil springs 120, the helical coil springs 120 are slightly shrunk with the deformation of the load cell 107, so that the load cell 107 is always contacted with the force transmitting portion 115.

At this time, the deformed amounts of the specimen 150, which are gradually changed in the vertical direction, that is, acting direction are taken as h which are variables. The forces of α which are variables and applied to the specimen 150 from the indenter 121 are also gradually changed, thereafter becomes stable. The forces of α are the same as the forces of β which are variables and applied to the load cell 107, so that it is possible to continuously determine the forces of α by continuously determining the forces of β.

The variations of ΔD of the distances of D measured continuously by the laser displacement meter 103 are sums of the deformed amounts of the load cell 107 and the specimen 150 in the vertical direction. Accordingly, the deformed amounts of h of the specimen 150 are obtained by subtracting the deformed amounts of h' of the load cell 107, which are determined in advance from the variations of ΔD of the distances of D Therefore, it is possible to continuously determine the deformed amounts of h of the specimen 150.

Further, by the computer 111, it is possible to find the dynamic characteristic of the specimen 150 by drawing up the graph showing the relation between the forces of α and the variations of h, as shown in FIG. 19.

For evaluating the dynamic characteristic of another specimen, the movable portion 139 is moved in the upper direction by the position adjusting member, so that the distance between the specimen 150 and the indenter 121 is made larger to exchange the specimen. Thereafter, the evaluation above-described is carried out.

According to the apparatus of the invention, it is possible to make the movable portion move and return by the position adjusting member. Accordingly, when the specimen is placed on the specimen table, it is possible to use the position adjusting member to make a space between the specimen table and the indenter, which is larger than a size of the specimen. Further, after the specimen is placed thereon, it is possible to use the position adjusting member to bring into contact the indenter to the specimen, so that it is possible to easily place the specimen and prepare for the evaluation.

In the above-described embodiments, the laser displacement meter is used for the distance measuring member, however, it is not limited to that. Another member which can measure values to determine the deformed amounts of the specimen can be used for the distance measuring member.

The indenter has the pyramidal shape in the top end portion, however, it can have another shape.

In addition, the position adjusting member can have another structure which can apply moving and returning forces to the movable portion.

From the foregoing description, one skilled in the art can easily ascertain the essential characteristics of this invention, and without departing from the spirit and scope thereof, can make various changes and modifications of the invention to adapt it to various usage and conditions.

The entire disclosure of Japanese Patent Applications No. 10-110140 filed on Apr. 6, 1998, No. 10-204376 filed on Jul. 3, 1998, and No. 10-200791 filed on Jul. 15, 1998 including specification, claims, drawings and summary are incorporated herein by reference in its entirety.

What is claimed is:

1. An apparatus for evaluating a dynamic characteristic of a specimen, which is installed in a hardness tester having a force applying member and a specimen table, the apparatus comprising:

an indenter;

a force transmitting portion that receives a force from the force applying member and transmits the force to the indenter to urge the indenter into pressing contact with the specimen placed on the specimen table;

a force measuring member for continuously determining forces of α applied to the specimen from the indenter;

a distance measuring member for continuously determining deformed amounts of h of the specimen in an acting direction of the forces of α;

wherein the force applying member displaces a movable portion, including the force transmitting portion, the force measuring member and the indenter, in an acting direction of the force, and when the force from the force applying member is applied to the force transmitting portion and displaces the movable portion, the indenter forms an indentation in the specimen, and the apparatus caries out an evaluation of the dynamic characteristic of the specimen based on (a) continuous values of the forces of $\alpha$ which are determined based on the measured values measured continuously by the force measuring member and (b) continuous values of the deformed amounts of h which are determined based on measured values measured continuously by the distance measuring member, and the apparatus further comprising
 a position adjusting member to adjust a position of the movable portion;
 wherein the position adjusting member comprises:
  a first axis;
  an arm capable of pitching pivotally on the first axis, the movable portion is movably connected to one end of the arm;
  a fixing plate attached to the other end of the arm;
  a receiving plate of which a position being fixed; and
  a clamping screw connected to the fixing plate, a screw portion of the clamping screw being screwed to the receiving plate,
   wherein when the clamping screw is clamped or loosened, the arm is pitched and the movable portion is freely moved and returned by a pitch of the arm.

2. The apparatus for evaluating a dynamic characteristic of a specimen as claimed in claim 1, wherein the force measuring member is a load cell and is disposed between the force transmitting portion and the indenter, the distance measuring member is a laser displacement meter and is disposed in the force transmitting portion, and further wherein variations of $\Delta D$ of distances of D are continuously determined by continuously measuring the distances of D between a fixed point of the laser displacement meter and a point of the force transmitting portion, and the apparatus further comprises a data processing equipment for continuously determining variations of $\Delta D$ of distances of D, and for continuously determining the deformed amounts of h by subtracting deformed amounts of h' of the load cell in the acting direction from the variations of $\Delta D$.

3. The apparatus for evaluating a dynamic characteristic of a specimen as claimed in claim 1, wherein the force measuring member is held by a holder which is detachably attached to the force transmitting portion, the holder is energised by an energising member to make the force measuring member be always contacted with the force transmitting portion.

4. The apparatus for evaluating a dynamic characteristic of a specimen as claimed in claim 1, further comprising a data processing equipment which draws up a graph showing a relation between the forces of a and the deformed amounts of h based on the measured values of the forces measured by the force measuring member and the measured values of distances of D measured by the distance measuring member.

5. The apparatus for evaluating a dynamic characteristic of a specimen as claimed in claim 1 the position adjusting member comprises:

a concave spherical washer, and
a convex spherical washer capable of moving rotatably for the concave spherical washer, at a connecting portion between the clamping screw and the arm.

6. An apparatus for evaluating a dynamic characteristic of a specimen, comprising:

an indenter;
a force transmitting means for receiving a force and for transmitting the force to the indenter to urge the indenter into pressing contact with the specimen;
a force measuring means for continuously determining forces of $\alpha$ applied to the specimen from the indenter;
a distance measuring means for continuously determining deformed amounts of h of the specimen in an acting direction of the forces of $\alpha$; and
a data processing means for continuously determining variations of $\Delta D$ of distances of D between a fixed point of the distance measuring means and a point of the force transmitting means, and for continuously determining the deformed amounts of h by subtracting deformed amounts of h' of the force measuring means in the acting direction from the variations of $\Delta D$.

* * * * *